US008450385B2

(12) United States Patent
Chopra et al.

(10) Patent No.: US 8,450,385 B2
(45) Date of Patent: May 28, 2013

(54) UREA-URETHANE GELLANT COMPOSITIONS WITH CONTROLLED MOLECULAR WEIGHT AND METHODS OF PREPARATION

(75) Inventors: Naveen Chopra, Oakville (CA); Michelle N. Chretien, Mississauga (CA); Barkev Keoshkerian, Thornhill (CA)

(73) Assignee: Xerox Corporation, Norwalk, CT (US)

( * ) Notice: Subject to any disclaimer, the term of this patent is extended or adjusted under 35 U.S.C. 154(b) by 64 days.

(21) Appl. No.: 12/974,083

(22) Filed: Dec. 21, 2010

(65) Prior Publication Data
US 2012/0157562 A1 Jun. 21, 2012

(51) Int. Cl.
C09D 11/10 (2006.01)

(52) U.S. Cl.
USPC ................................................ 522/78; 560/25

(58) Field of Classification Search
None
See application file for complete search history.

(56) References Cited

U.S. PATENT DOCUMENTS

| | | | |
|---|---|---|---|
| 4,830,671 A | 5/1989 | Frihart et al. | |
| 5,231,135 A | 7/1993 | Machell et al. | |
| 5,496,879 A | 3/1996 | Griebel et al. | |
| 5,621,022 A | 4/1997 | Jaeger et al. | |
| 5,783,657 A | 7/1998 | Pavlin et al. | |
| 6,111,055 A | 8/2000 | Berger et al. | |
| 6,221,137 B1 | 4/2001 | King et al. | |
| 6,472,523 B1 | 10/2002 | Banning et al. | |
| 6,476,219 B1 | 11/2002 | Duff et al. | |
| 6,547,380 B2 | 4/2003 | Smith et al. | |
| 6,576,747 B1 | 6/2003 | Carlini et al. | |
| 6,576,748 B1 | 6/2003 | Carlini et al. | |
| 6,590,082 B1 | 7/2003 | Banning et al. | |
| 6,646,111 B1 | 11/2003 | Carlini et al. | |
| 6,663,703 B1 | 12/2003 | Wu et al. | |
| 6,673,139 B1 | 1/2004 | Wu et al. | |
| 6,696,552 B2 | 2/2004 | Mayo et al. | |
| 6,713,614 B2 | 3/2004 | Carlini et al. | |
| 6,726,755 B2 * | 4/2004 | Titterington et al. | 106/31.29 |
| 6,755,902 B2 | 6/2004 | Banning et al. | |
| 6,821,327 B2 | 11/2004 | Jaeger et al. | |
| 6,958,406 B2 | 10/2005 | Banning et al. | |
| 7,053,227 B2 | 5/2006 | Jaeger et al. | |
| 7,270,408 B2 | 9/2007 | Odell et al. | |
| 7,381,831 B1 | 6/2008 | Banning et al. | |
| 7,427,323 B1 | 9/2008 | Birau et al. | |
| 7,625,956 B2 | 12/2009 | Odell et al. | |
| 7,632,546 B2 * | 12/2009 | Odell et al. | 427/466 |
| 2001/0044553 A1 | 11/2001 | Kabashima et al. | |
| 2006/0119686 A1 | 6/2006 | Odell | |
| 2006/0122415 A1 * | 6/2006 | Carlini et al. | 560/25 |
| 2006/0158491 A1 | 7/2006 | Belelie et al. | |
| 2006/0158492 A1 | 7/2006 | Odell et al. | |
| 2007/0123606 A1 | 5/2007 | Toma et al. | |

OTHER PUBLICATIONS

U.S. Appl. No. 12/765,138 to Chopra et al. (filed Apr. 22, 2010).
U.S. Appl. No. 12/765,148 to Chopra et al. (filed Apr. 22, 2010).
U.S. Appl. No. 12/765,341 to Chopra et al. (filed Apr. 22, 2010).
U.S. Appl. No. 12/765,309 to Chopra et al. (filed Apr. 22, 2010).
"Dimer Acids," Kirk-Othmer Encyclopedia of Chemical Technology, vol. 8, 4th Edition, pp. 223-237, 1992.

* cited by examiner

*Primary Examiner* — Randy Gulakowski
*Assistant Examiner* — Jeffrey Washville
(74) *Attorney, Agent, or Firm* — Oliff & Berridge, PLC

(57) ABSTRACT

Urea-urethane gellant compositions and methods of preparing the urea-urethane gellant compositions. The method includes adding an isocyanate, an alcohol or a diamine, and a solvent to a reaction vessel; stirring the reaction vessel at either ambient or elevated temperature; isolating an intermediate product from the reaction vessel; and converting the intermediate product to the organic gellant. The urea-urethane gellants are prepared in a manner to control the molecular weight and control the formation of dimers and trimers. The gellants may be used in curable gel inks.

16 Claims, No Drawings

UREA-URETHANE GELLANT COMPOSITIONS WITH CONTROLLED MOLECULAR WEIGHT AND METHODS OF PREPARATION

TECHNICAL FIELD

This disclosure is generally directed to gellant compositions used in curable inks, and methods for producing such gellants, for use in forming and developing images of good quality. More specifically, this disclosure is directed to urea-urethane based gellants with discrete repeat units and a narrow distribution of molecular weight. This disclosure is also directed to methods of forming such urea-urethane gellant in a desired oligomer size (dimers and trimers). Such gellants are useful, for example, in curable inks that may be used in ink jet printing systems.

BACKGROUND

U.S. Patent Application Publication No. 2006/0158491 to Belelie et al. discloses non-gellant ink jet ink compositions that comprise wax backbones containing a functionalized group, and methods of forming an image with such inks. Some disclosed ink jet ink compositions are cationically curable.

U.S. Patent Application Publication No. 2006/0158492 to Odell et al. discloses non-gellant ink jet ink compositions that can be cured via at least two different polymerization routes, including radical and cationic polymerization routes, and methods of forming an image with such inks by advantageously utilizing the different polymerization routes. Also described are non-gellant ink jet ink compositions that can be cured by a single polymerization route and that contain two photoinitiator systems that absorb radiation at different wavelengths.

U.S. Pat. No. 7,625,956 to Odell et al., which is incorporated herein by reference in its entirety, discloses a phase change ink composition comprising a colorant, a photoinitiator, and an ink vehicle. The ink vehicle comprises a radically curable monomer compound and an amide gellant compound of the formula

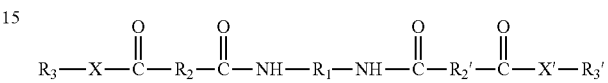

in which the reference further defines the specific substituents.

U.S. patent application Ser. Nos. 12/765,138, 12/765,148, and 12/765,341 to Chopra et al., the disclosures of which are incorporated herein by reference in their entirety, disclose a phase change ink composition comprising a colorant, a photoinitiator, and an ink vehicle. The ink vehicle comprises a radically curable monomer compound and an amide gellant compound of the formula

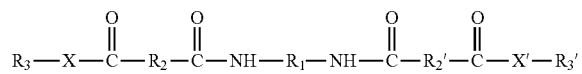

in which the references further define the specific substituents.

U.S. patent application Ser. No. 12/765,309 to Chopra et al., which is incorporated by reference, discloses a curable ink composition for three dimensional printing comprising an optional colorant and a phase change ink vehicle comprising a radiation curable monomer or prepolymer, a photoinitiator, a reactive wax, and a gellant upon a print region surface, successively depositing additional amounts of the ultraviolet curable phase change ink composition to create a three-dimensional object, and curing the ultraviolet curable phase change ink composition. The ink vehicle comprises a radically curable monomer compound and an amide gellant compound of the formula

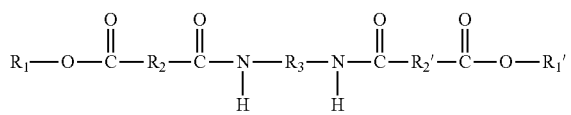

in which the reference further defines the specific substituents.

U.S. Patent Application Publication No. 2007/0123606 to Toma et al. discloses a phase change ink comprising a colorant, an initiator, and a phase change ink carrier. The ink vehicle comprises a radically curable monomer compound and an amide gellant compound as further defined in the reference.

Ink jetting devices are known in the art, and thus extensive description of such devices is not required herein. As described in U.S. Pat. No. 6,547,380, incorporated herein by reference in its entirety, ink jet printing systems generally are of two types: continuous stream and drop-on-demand.

In continuous stream ink jet systems, ink is emitted in a continuous stream under pressure through at least one orifice or nozzle. The stream is perturbed, causing it to break up into droplets at a fixed distance from the orifice. At the break-up point, the droplets are charged in accordance with digital data signals and passed through an electrostatic field that adjusts the trajectory of each droplet in order to direct it to a gutter for recirculation or a specific location on a recording medium. In drop-on-demand systems, a droplet is expelled from an orifice directly to a position on a recording medium in accordance with digital data signals. A droplet is not formed or expelled unless it is to be placed on the recording medium.

There are at least three types of drop-on-demand ink jet systems. One type of drop-on-demand system is a piezoelectric device that has as its major components an ink filled channel or passageway having a nozzle on one end and a piezoelectric transducer near the other end to produce pressure pulses. Another type of drop-on-demand system is known as acoustic ink printing. An acoustic beam exerts a radiation pressure against objects upon which it impinges. Thus, when an acoustic beam impinges on a free surface (i.e., liquid/air interface) of a pool of liquid from beneath, the radiation pressure which it exerts against the surface of the pool may reach a sufficiently high level to release individual droplets of liquid from the pool, despite the restraining force of surface tension. Focusing the beam on or near the surface of the pool intensifies the radiation pressure it exerts for a given amount of input power. Still another type of drop-on-demand system is known as thermal ink jet, or bubble jet, and produces high velocity droplets. The major components of this type of drop-on-demand system are an ink filled channel having a nozzle on one end and a heat generating resistor near the nozzle. Printing signals representing digital information originate an electric current pulse in a resistive layer within each ink passageway near the orifice or nozzle, causing the ink vehicle (usually water) in the immediate vicinity to vaporize almost instantaneously and create a bubble. The ink at the orifice is forced out as a propelled droplet as the bubble expands.

Phase change inks, also referred to as hot-melt inks, may be used in ink jet printing. In general, phase change inks are in a solid or semi-solid phase at, for example, ambient temperature, but exist in the liquid phase at the elevated operating temperature of an ink jet printing device. At the jet operating temperature, droplets of liquid ink are ejected from the printing device and, when the ink droplets contact the surface of the recording substrate, either directly or via an intermediate heated transfer belt or drum, they quickly solidify to form a predetermined pattern of solidified ink drops. Phase change inks have been used in other printing technologies, such as gravure printing, as disclosed in, for example, U.S. Pat. No. 5,496,879, the disclosure of which is totally incorporated herein by reference. Phase change inks have also been used for applications such as postal marking, industrial marking, and labeling.

Phase change inks are desirable for ink jet printers because they remain in a solid or semi-solid phase at room temperature during shipping, long term storage, and the like. In addition, the problems associated with nozzle clogging as a result of ink evaporation with liquid ink jet inks are largely eliminated, thereby improving the reliability of the ink jet printing. Further, in phase change ink jet printers wherein the ink droplets are applied directly onto the final recording substrate (for example, paper, transparency material, and the like), the droplets solidify immediately upon contact with the substrate, so that migration of ink along the printing medium is prevented and dot quality is improved.

One problem encountered when preparing ester-terminated polyamide gellants such as those disclosed above is the variability of molecular weight ($M_w$) distribution of organoamide gellant precursors, which are oligomeric molecules. Variable $M_w$ distribution leads to variability in the gel inks formed during mass production. Variable molecular weight distribution can lead to undesirable variation in the gel strength and viscosity. In particular, the gel may be too soft or too stiff, which can introduce problems in the print process or image quality.

A need remains for improved gellants in phase change inks, for example for gellants that exhibit increased viscosity and a narrow molecular weight range. A need, therefore, also remains for methods of producing gellants with a narrow molecular weight range and control of oligomer size.

SUMMARY

Detailed herein are organic gellants with a narrow molecular weight distribution. These gellants may be prepared by adding an isocyanate, an alcohol or a diamine, and a solvent to a reaction vessel; stirring the contents of the reaction vessel; isolating an intermediate product from the reaction vessel; and converting the intermediate product to the organic gellant in a subsequent reaction.

Detailed herein are urea-urethane gellants having a molecular weight distribution of less than 2; and a viscosity of about 8 mPa·s to about $2.20 \times 10^5$ mPa·s at a temperature of about 30° C. to about 90° C. The gellants are suitable for formulation into radiation curable phase change inks and overcoat compositions.

Embodiments

This disclosure is not limited to the particular embodiments described herein, and some components and processes may be varied by one of ordinary skill, based on this disclosure.

In this specification and the claims that follow, singular forms such as "a," "an," and "the" include plural forms unless the content clearly dictates otherwise. All ranges disclosed herein include, unless specifically indicated, all endpoints and intermediate values. In addition, reference may be made to a number of terms that shall be defined as follows:

The term "functional group" refers, for example, to a group of atoms arranged in a way that determines the chemical properties of the group and the molecule to which it is attached. Examples of functional groups include halogen atoms, hydroxyl groups, carboxylic acid groups, and the like.

The term "curable" describes, for example, a material that may be cured via polymerization or is chain extendable, including for example free radical polymerization or chain extension, cationic polymerization or chain extension, and/or in which polymerization is photoinitiated with a radiation-sensitive photoinitiator. The term "radiation-curable" refers, for example, to all forms of curing upon exposure to a radiation source, including light and heat sources and including in the presence or absence of initiators. Exemplary radiation-curing techniques include curing using ultraviolet (UV) light, for example having a wavelength of 200-400 nm, or using visible light, optionally in the presence of photoinitiators and/or sensitizers, curing using electron-beam radiation, optionally in the absence of photoinitiators, curing using thermal curing in the presence or absence of high-temperature thermal initiators (and which may be largely inactive at the jetting temperature), and appropriate combinations thereof.

As used herein, the term "viscosity" refers to a complex viscosity, which is the typical measurement provided by a mechanical rheometer capable of subjecting a sample to a steady shear strain or a small amplitude sinusoidal deformation. In this type of instrument, the shear strain is applied by the operator to the motor and the sample deformation (torque) is measured by the transducer. Alternatively, a controlled-stress instrument, where the shear stress is applied and the resultant strain is measured, may be used. Such a rheometer provides a periodic measurement of viscosity at various plate rotation frequencies, ω, rather than the transient measurement of, for instance, a capillary viscometer. The reciprocating plate rheometer is able to measure both the in phase and out of phase fluid response to stress or displacement. The complex viscosity, $\eta^*$, is defined as $\eta^* = \theta' - i\eta''$; where $\eta' = G''/\omega$, $\eta'' = G'/\omega$ and i is $\sqrt{-1}$. Alternatively a viscometer that can measure only the transient measurement of, for instance, a capillary or shear viscosity can also be used.

"Optional" or "optionally" refer, for example, to instances in which subsequently described circumstance may or may not occur, and include instances in which the circumstance occurs and instances in which the circumstance does not occur.

The terms "one or more" and "at least one" refer, for example, to instances in which one of the subsequently described circumstances occurs, and to instances in which more than one of the subsequently described circumstances occurs.

Disclosed are urea-urethane gellants for use in ink and overcoat compositions, and methods for producing such gellants.

In addition to a gellant, such ink compositions may comprise, for example, a cationically curable monomer, a cationic photoinitiator and, optionally, a radically curable monomer and, further optionally, a free-radical photoinitiator. Compositions that include both a cationically curable component and a radically curable component are referred to herein as "hybrid" compositions. The hybrid compositions may comprise a radically curable monomer and a free-radical photoinitiator for catalyzing free-radical curing upon exposure to radiation, in addition to a gellant, a cationically curable monomer and a cationic photoinitiator for catalyzing cationic curing upon exposure to radiation.

For an ink composition, the composition may further comprise a colorant, such as a pigment, dye, mixture of pigments, mixture of dyes, or mixture of pigments and dyes, present in an amount from about 0.5% to about 15% by weight of the composition, such as from about 1% to about 10% or from about 3% to about 8% by weight of the composition. The colorant may be present in an amount from about 0.5% to about 15% by weight of the composition, such as from about 9% to about 15% or from about 11% to about 14% by weight of the composition. For an overcoat composition, the composition is substantially free of colorant. By "substantially free of colorant," it is meant that the composition comprises a colorant present in an amount less than about 0.5% by weight of the composition. The compositions are radiation curable compositions, such as UV curable compositions. The compositions may also optionally include a stabilizer, a surfactant, or other additives.

Urea-Urethane Gellants

As a gellant, urea and urethane compounds may be used. By gel-like behavior is meant that the compounds, when dissolved in a solvent (such as radiation curable liquid monomers), undergo a relatively sharp increase in viscosity over a relatively narrow temperature range. Some compounds as disclosed herein undergo a change in viscosity of at least about $10^3$ mPa·s, at least about $10^5$ mPa·s, or at least about $10^6$ mPa·s, over a temperature range of at least about 5° C., at least about 10° C., or at least about 30° C., although the viscosity change and the temperature range can be outside of these ranges, and compounds that do not undergo changes within these ranges are also included herein.

As a gellant, urea-urethane dimers and trimers are useful in inks. The rheology of inks comprising urea-urethane dimers and trimers exhibit rapid phase change as a function of temperature. The use of gelators with novel and unique gellation profiles widens the scope of ink properties that can be achieved.

The gellant may comprise a compound of the formula (I):

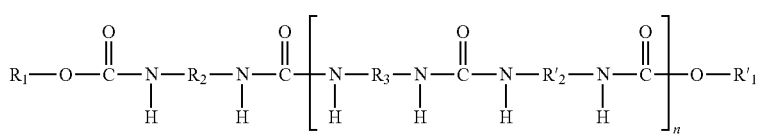

(I)

where:

$R_1$ and $R_1'$ are the same or different from each other and are selected from the following non-reactive aromatic groups:

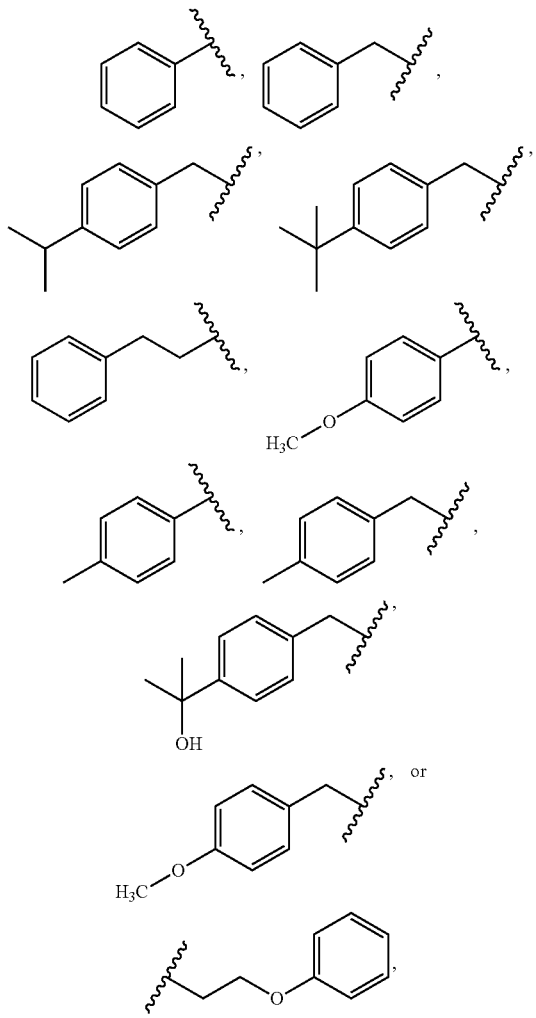

wherein ∿∿∿ represents the point of attachment of the $R_1$ and $R_1'$ group.

In some embodiments, $R_1$ and $R_1'$ are the same and are selected from the formulas:

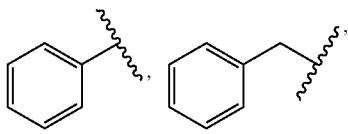

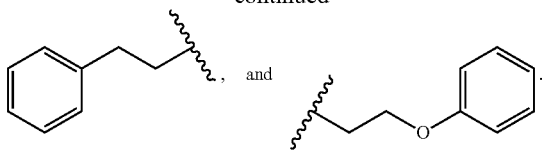

In one specific embodiment, $R_1$ and $R_1'$ are each of the formula

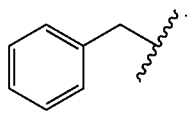

$R_2$ and $R_2'$ are the same or different, and are each independently selected from:

(i) an alkylene group (wherein an alkylene group is a divalent aliphatic group or alkyl group, including linear and branched, saturated and unsaturated, cyclic and acyclic, and substituted and unsubstituted alkylene groups; and wherein heteroatoms, such as oxygen, nitrogen, sulfur, silicon, phosphorus, boron, and the like either may or may not be present in the alkylene group) having from about 2 to about 100 carbon atoms, such as at least from about 2 to about 100, or from about 2 to about 60 or from about 2 to about 50;

(ii) an arylene group (wherein an arylene group is a divalent aromatic group or aryl group, including substituted and unsubstituted arylene groups, and wherein heteroatoms, such as oxygen, nitrogen, sulfur, silicon, phosphorus, boron, and the like either may or may not be present in the arylene group) having from about 5 to about 100 carbon atoms, such as from about 6 to about 60, or from about 6 to about 50;

(iii) an arylalkylene group (wherein an arylalkylene group is a divalent arylalkyl group, including substituted and unsubstituted arylalkylene groups, wherein the alkyl portion of the arylalkylene group can be linear or branched, saturated or unsaturated, and cyclic or acyclic, and wherein heteroatoms, such as oxygen, nitrogen, sulfur, silicon, phosphorus, boron, and the like either may or may not be present in either the aryl or the alkyl portion of the arylalkylene group) having from about 5 to about 100 carbon atoms, such as from about 6 to about 60, or from about 6 to about 50; and (iv) an alkylarylene group (wherein an alkylarylene group is a divalent alkylaryl group, including substituted and unsubstituted alkylarylene groups, wherein the alkyl portion of the alkylarylene group can be linear or branched, saturated or unsaturated, and cyclic or acyclic, and wherein heteroatoms, such as oxygen, nitrogen, sulfur, silicon, phosphorus, boron, and the like either may or may not be present in either the aryl or the alkyl portion of the alkylarylene group) having from about 5 to about 100 carbon atoms, such as from about 6 to about 60, or from about 6 to about 50.

Unless otherwise specified, the substituents on the substituted alkyl, aryl, alkylene, arylene, arylalkylene, and alkylarylene groups disclosed above and hereinafter may be selected from halogen atoms, cyano groups, pyridine groups, pyridinium groups, ether groups, aldehyde groups, ketone groups, ester groups, amide groups, carbonyl groups, thiocarbonyl groups, sulfide groups, nitro groups, nitroso groups, acyl groups, azo groups, urethane groups, urea groups, mixtures thereof, and the like. Optionally, two or more substituents may be joined together to form a ring.

In some embodiments, $R_2$ and $R_2'$ have the formula

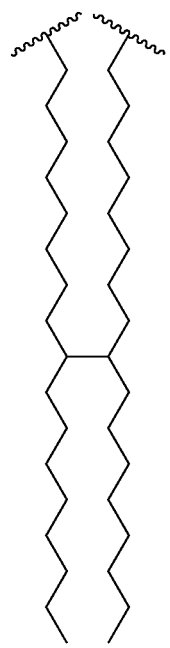 [SMILES: *CCCCCCCCC(CCCCCCCC)C(CCCCCCCC)CCCCCCCC*]

wherein ~~~ represents the point of attachment.

$R_3$ is:

(i) an alkylene group having from about 2 to about 80 carbon atoms, such as, for example, at least about 2 carbon atoms, or from about 30 to about 60 carbon atoms or from about 36 to about 50 carbon atoms;

(ii) an arylene group having from about 2 to about 50 carbon atoms, such as, for example, at least about 2 carbon atoms, or from about 30 to about 60 carbon atoms or from about 36 to about 50 carbon atoms;

(iii) an arylalkylene group having from about 6 to about 50 carbon atoms such as, for example, at least about 2 carbon atoms, or from about 30 to about 60 carbon atoms or from about 36 to about 50 carbon atoms; or (iv) an alkylarylene group having from about 6 to about 50 carbon atoms, such as, for example, at least about 2 carbon atoms, or from about 30 to about 60 carbon atoms or from about 36 to about 50 carbon atoms.

n is an integer from 1 to 7, or from 2 to 5, or from 1 to 3.

The gellant may be a urea-urethane dimer or trimer. Exemplary gellant compounds include:

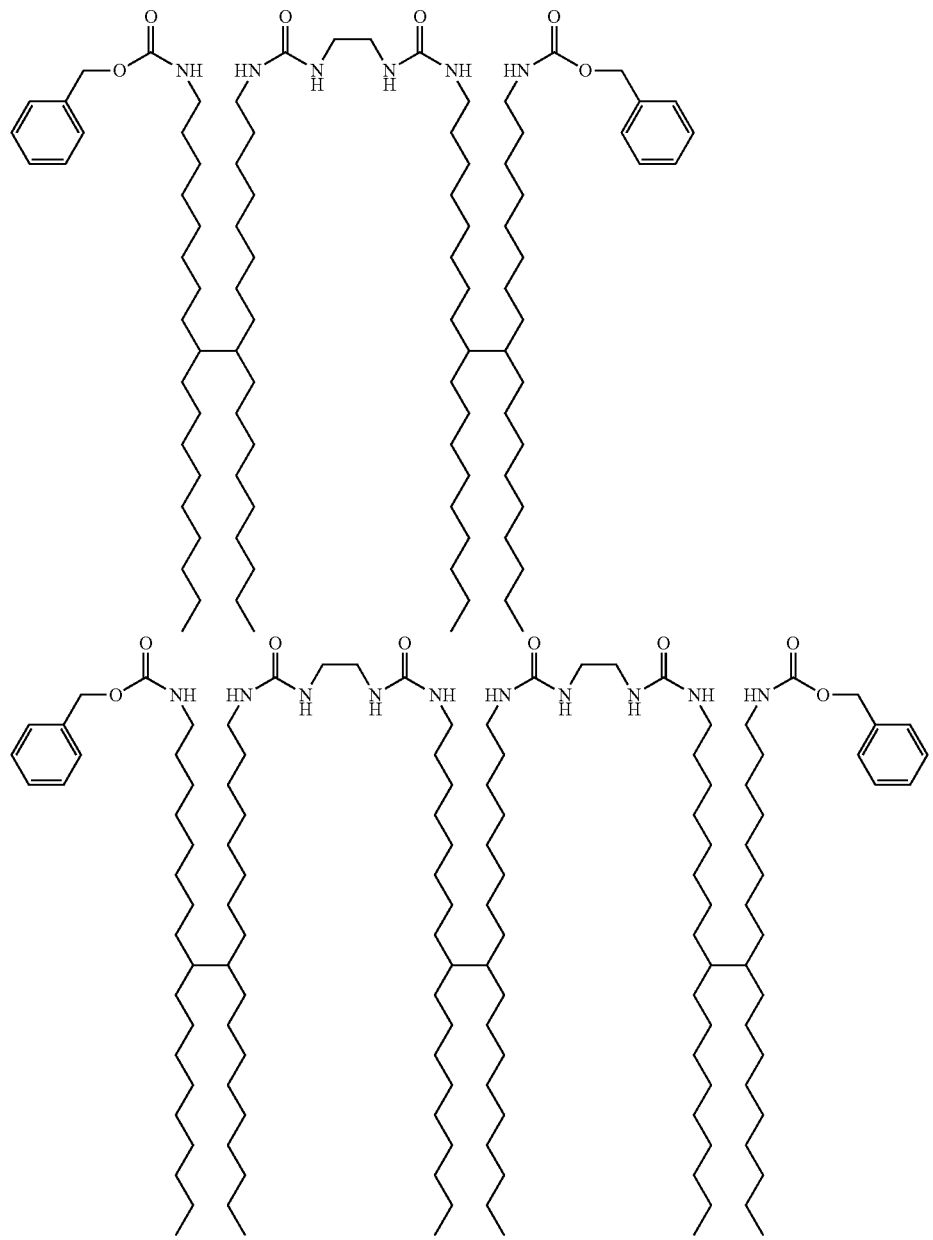

The curable ink compositions (or other colored or colorless compositions) disclosed herein may form a semi-solid gel at a first temperature. For example, when the gellant is incorporated into a phase change ink, this temperature is below the specific temperature at which the ink is jetted. The semi-solid gel phase is a physical gel that exists as a dynamic equilibrium comprising one or more solid gellant molecules and a liquid solvent. The semi-solid gel phase is a dynamic networked assembly of molecular components held together by non-covalent interactions such as hydrogen bonding, Van der Waals interactions, aromatic non-bonding interactions, ionic or coordination bonding, London dispersion forces, or the like, which, upon stimulation by physical forces, such as temperature, mechanical agitation, or the like, or chemical forces, such as pH, ionic strength, or the like, can undergo reversible transitions from liquid to semi-solid state at the macroscopic level. The solutions containing the gellant molecules exhibit a thermally reversible transition between the semi-solid gel state and the liquid state when the temperature is varied above or below the gel point of the solution. This reversible cycle of transitioning between semi-solid gel phase and liquid phase can be repeated many times in the solution formulation.

The phase change nature of the gellant may be used to cause a rapid viscosity increase in the jetted ink composition following jetting of the ink to the substrate. In particular, jetted ink droplets may be pinned into position on a receiving substrate with a cooler temperature than the ink-jetting temperature of the ink composition through the action of a phase-change transition.

The colored or colorless composition may include the gellant in any suitable amount, such as from about 1% to about 50% by or from about 10% to about 40% or from about 15% to about 35% or from about 5% to about 20% by weight of the composition.

Preparation of Gellant

By controlling the reaction, it is possible to prepare a urea-urethane gellant that is a dimer or a trimer. Achieving a controlled reaction may be done in at least two ways. First, by taking advantage of differential reactivity rate in formation of urethanes (heat required) and ureas (room temperature). Second, a controlled reaction may be achieved by coupling monofunctionalized compounds with difunctional compounds. As used herein, "monofunctionalized compounds" refers to compounds where one end of the compound is blocked to control reactivity.

One scheme for a controlled reaction is illustrated below:

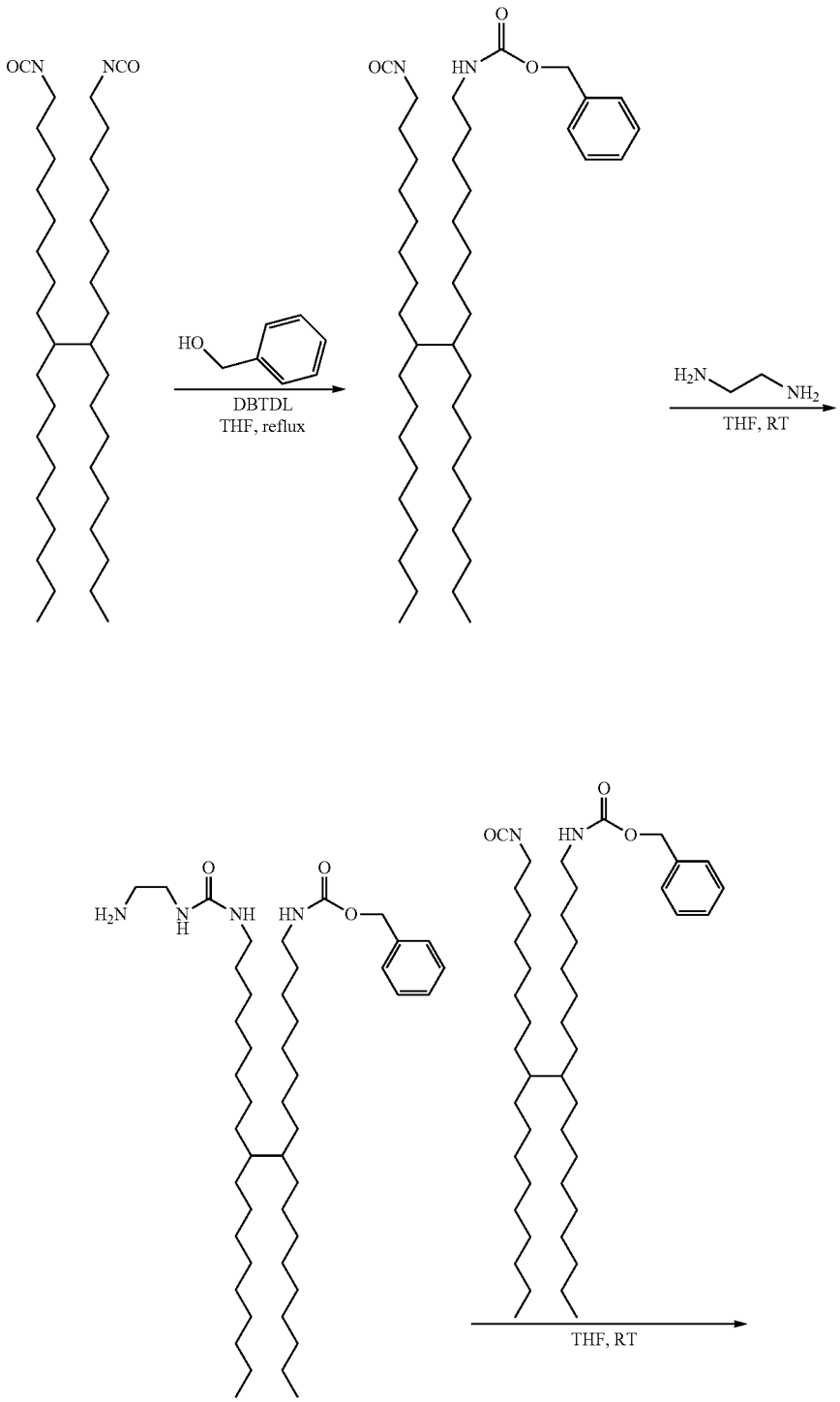

-continued
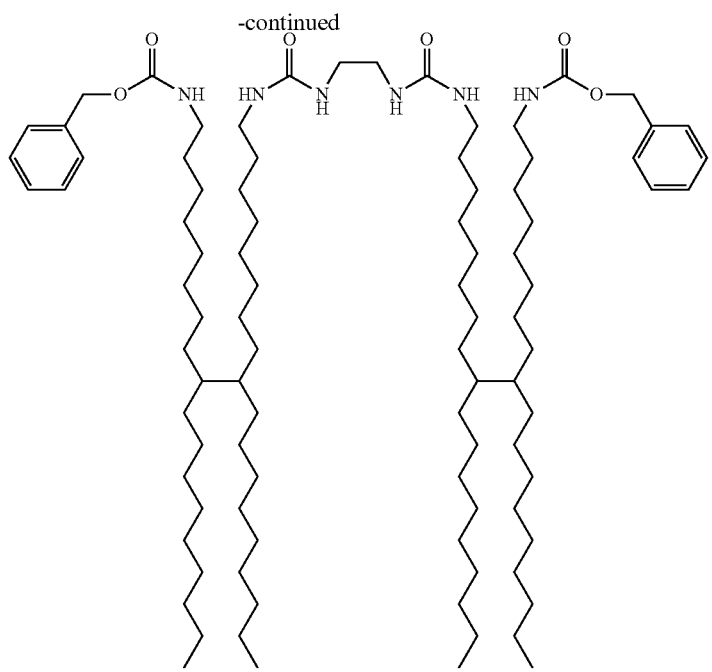
A second scheme for a controlled reaction is illustrated below:
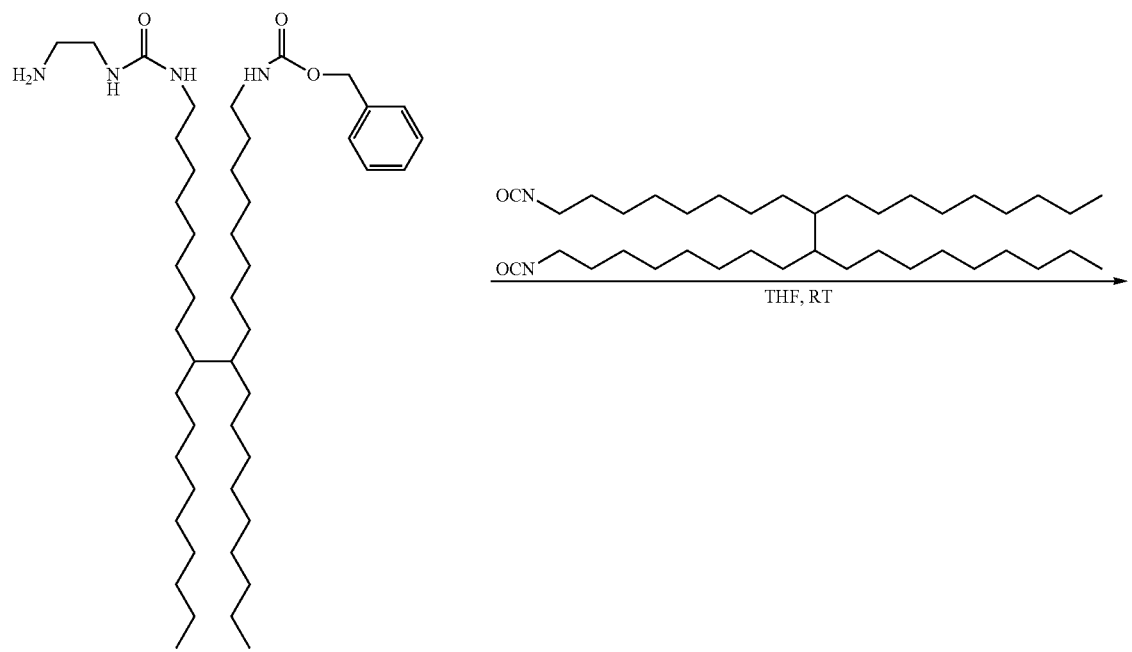

-continued

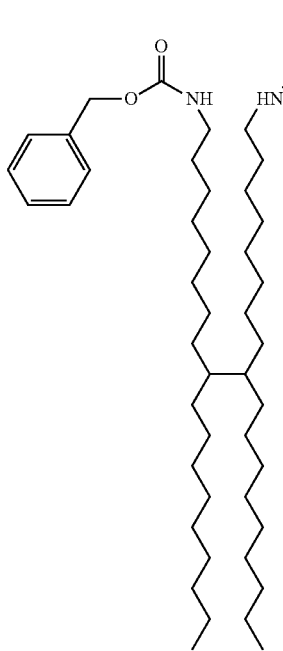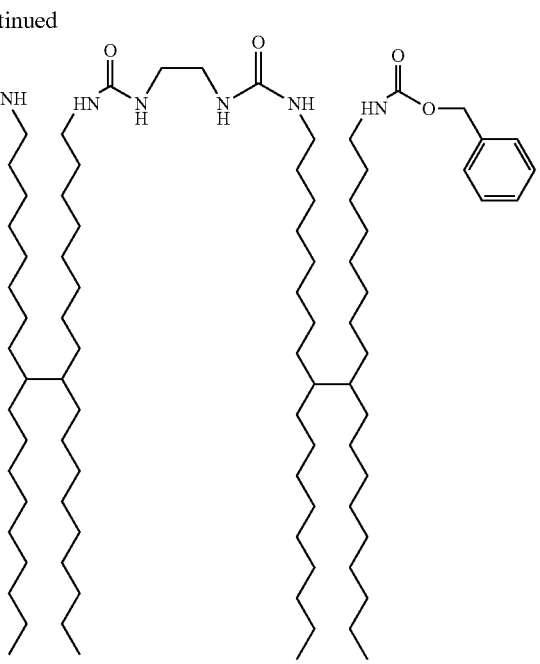

Compounds as disclosed herein may be prepared by any desired or effective method as long as at least one urea group and at least one urethane group are formed. For example, in one embodiment, about 1 molar equivalents of an isocyanate having at least two isocyanate groups is a starting material. One of the isocyanate groups is reacted with an alcohol to create a urethane linkage. The remaining isocyanate group of this first molecule is then reacted with a second compound containing a diamine functional group to create a urea linkage. This intermediate product now has a urethane group, a urea group, and a free amine group. When this intermediate product is reacted with a molecule containing a urethane and an unreacted isocyanate, a dimer (n=1) is formed. When the intermediate product is reacted with a molecule containing 2 unreacted isocyanates, a trimer (n=2) is formed.

The starting isocyanate is not particularly limited so long as it has two or more isocyanate groups. Suitable starting isocyanates include, for example, p-phenylene diisocyanate, 2,5-dimethoxybenzene-1,4-diisocyanate, 2,4-toluene diisocyanate, 2,6-toluene diisocyanate, diphenylmethane diisocyanate, o-tolidine diisocyanate, diphenyl ether diisocyanate, 1,5-naphthylene diisocyanate, dianisidine diisocyanate, 9-ethylcarbazole-3,6-diisocyanate, 3,3'-dimethyl-4,4'-diphenylmethane diisocyanate, hexamethylene diisocyanate, isophorone diisocyanate, triphenylmethane triisocyanate, tris (4-phenylisocyanate) thiophosphate, 4,4',4"-triisocyanato-2,5-dimethoxytriphenylamine, 4,4',4"-triisocyanatotriphenylamine, m-xylylene diisocyanate, lysine diisocyanate, dimer acid diisocyanate, isopropylidene bis-4-cyclohexyl-isocyanate, dicyclohexylmethane diisocyanate, and methylcyclohexane diisocyanate. As the starting isocyanate, there may also be used diisocyanate dimers such as N,N'-(4,4'-dimethyl-3,3'-dipheny-1-diisocyanato)urethodione, a toluene diisocyanate dimer; and diisocyanate trimers such as 4,4',4"-trimethyl-3, 3',3"-triisocyanato-2,4,6-triphenylcyanurate. There may also be used water adduct isocyanates of toluene diisocyanate, diphenyl-methane diisocyanate and the like, such as 1,3-bis (3-isocyanato-4-methylphenyl)urea; polyol adducts such as trimethylolpropane adduct of toluene diisocyanate; and amine adducts.

As the amine compound that is reacted with the starting isocyanate for the urea-urethane compound to form one or more urea groups, any compound may be used so long as it has at least two amino groups. Examples of suitable diamines include ethylenediamine (EDA), 1,2-diaminopropane, 1,3-diaminopropane, 1,4-diaminobutane, 1,2-diamino-2-methylpropane, 1,3-diaminopentane, 1,5-diaminopentane, 2,2-dimethyl-1,3-propanediamine, 1,6-hexanediamine (also known as hexamethylenediamine, HMDA), 2-methyl-1,5-pentanediamine, 1,7-diaminoheptane, 1,8-diaminooctane, 2,5-dimethyl-2,5-hexanediamine, 1,9-diaminononane, 1,10-diaminodecane, 1,12-diaminododecane, diaminophenanthrene (all isomers, including 9,10), 4,4'-methylenebis(cyclohexylamine), 2,7-diaminofluorene, phenylene diamine (1,2; 1,3 and/or 1,4 isomers), adamantane diamine, 2,4,6-trimethyl-1, 3-phenylenediamine, 1,3-cyclohexanebis(methylamine), 1,8-diamino-p-menthane, 2,3,5,6-tetramethyl-1,4-phenylenediamine, diaminonaphthalene (all isomers, including 1,5; 1,8; and 2,3), 4-amino-2,2,6,6-tetramethylpiperidine, xylene diamine, naphthalene diamine, diethylenetriamine (DETA) and triethylenetetraamine (TETA), bis(aminoethyl)-N,N'-piperazine, bis(aminopropyl)-N,N'-piperazine, N-ethylethylenediamine, and 1-(2-aminoethyl)piperazine, 1,2-diamino-2-methylpropane, 1,3-diaminopentane, 1,5-diaminopentane, 2,2-dimethyl-1,3-propanediamine, 1,6-hexanediamine (also known as hexamethylenediamine, HMDA), 2-methyl-1,5-pentanediamine, 1,7-diaminoheptane, 1,8-diaminooctane, 2,5-dimethyl-2,5-hexanediamine, 1,9-diaminononane, 1,10-diaminodecane, 1,12-diaminododecane, diaminophenanthrene (all isomers, including 9,10), 4,4'-methylenebis(cyclohexylamine), 2,7-diaminofluorene, phenylene diamine (1,2; 1,3 and/or 1,4 isomers), adamantane diamine, 2,4,6-trimethyl-1,3-phenylenediamine, 1,3-cyclohexanebis(methylamine), 1,8-diamino-p-menthane, 2,3,5,6-tetramethyl-1,4-phenylenediamine, diaminonaphthalene (all isomers, including 1,5; 1,8; and 2,3), 4-amino-2,2,6,6-tetramethylpiperidine, xylene diamine, naphthalene diamine, and polyether diamines. Other diamines include alkylene diamines, such as those having up to 6 carbon atoms such as ethylene diamine or hexamethylene diamine.

Suitable OH group-containing compounds include, for example, 1-dodecanol, 1-tetradecanol, 1-hexadecanol (cetyl alcohol), 1-octadecanol (stearyl alcohol), 1-eicosanol (arachidyl alcohol) and 1-docosanol (behenyl alcohol), and 2-hexadecyloctadecanol. Suitable OH group-containing compounds also include a so-called Guerbet alcohol. Guerbet alcohols have the general formula H—C(Ra)(Rb)—CH$_2$—OH wherein Ra and Rb may be the same or different and may represent a C$_{6-12}$ hydrocarbon group. Suitable OH-group containing compounds also include alcohols with aromatic groups selected from the following non-reactive aromatic groups:

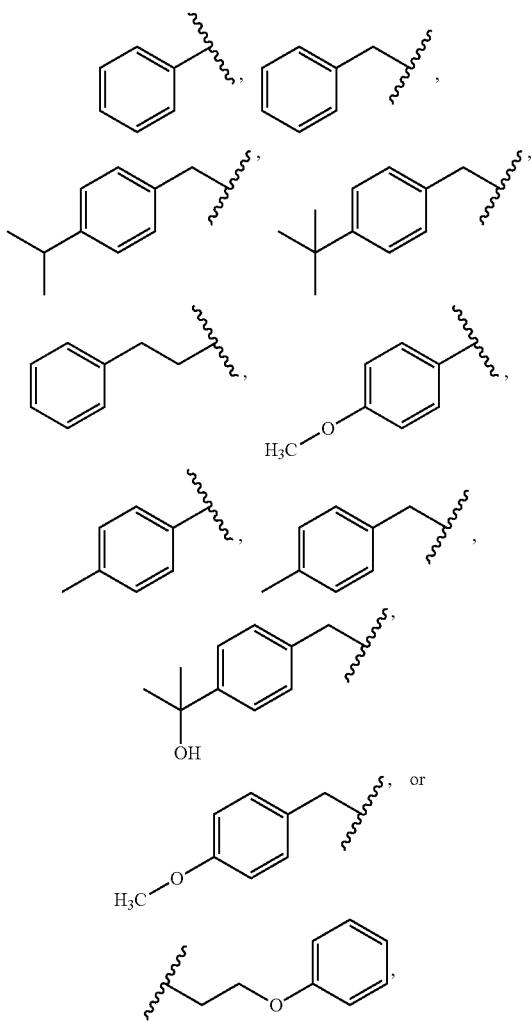

wherein ∿∿∿ represents the point of attachment.

The reaction temperature at which an isocyanate is reacted with a hydroxy compound and/or an amino compound to form one or more urethane groups and/or one or more urea groups may be from about 0° C. to about 300° C., or from about 5° C. to about 200° C., or from about 10° C. to about 150° C., or from about 10° C. to about 30° C. The reaction temperature is properly adjusted depending on the desired type of functional group created (urea or urethane). It is also possible to carry out the reaction at different temperatures suitable for the polyisocyanate compound, hydroxy compound and amino compound selected. For ureas, the reaction may take place at temperatures of up to about 60° C. For urethanes, the reaction may take place at temperatures up to about 150° C.

The reaction may also take advantage of coupling mono-functionalized compounds with difunctional compounds.

In one embodiment, to the resulting reaction mixture may be added about two molar equivalents of an identical aromatic end-cap molecule having the formula R$_1$—OH. In another embodiment, to the resulting reaction mixture can be added about one molar equivalent of a first end-cap molecule which is an aromatic alcohol having the formula R$_1$—OH as described herein.

The ingredients may be mixed together in the sequence just described and a one pot reaction may be employed. For example, the starting isocyanate can be added to a 0.5 liter round bottomed flask equipped with a magnetic stir bar, followed by solvent, such as THF, with stirring. A catalyst, such as dibutyltin dilaurate (DBTDL), can be added.

Next, in one embodiment, a single species of end-cap molecule can be added to the reaction mixture containing the isocyanate. Alternately, in another embodiment, a first species of end-cap molecule being an aromatic alcohol and a second species of end-cap molecule that is different from the aromatic alcohol can be added simultaneously to the reaction mixture.

The reaction mixture containing the isocyanate and the single end-cap component or the mixed end-cap components can be allowed to stir overnight at room temperature. The reaction contents can then be filtered to remove the by-product. The filtrate can be concentrated on a rotary evaporator resulting in a urea-urethane gellant. The solid residue can be dried in a vacuum oven, such as for about 2 hours at about 90° C., to remove residual solvent from the urea-urethane gellant.

The catalyst and the isocyanate are present in any desired or effective relative amounts. The catalyst and the isocyanate may be present in an amount of at least about 0.05 mole of catalyst per every 1 mole of isocyanate, or at least about 0.1 mole of catalyst per every 1 mole of isocyanate, or at least about 0.2 mole of catalyst per every 1 mole of isocyanate, or no more than about 1 mole of catalyst per every 1 mole of isocyanate.

The end-cap molecule may be present in any desired or effective relative amounts close to 1:1 ratio of diisocyanate to alcohol. For example, where R$_1$ and R$_1$' are the same and comprise an aromatic alcohol, in one embodiment, at least about 1.2 moles of aromatic alcohol per every 1 mole of diisocyanate, or at least about 1.1 moles of aromatic alcohol per every 1 mole of isocyanate, or at least about 1 mole of aromatic alcohol per every 1 mole of isocyanate. Where R$_1$ and R$_1$' are two different species, the combined total amount of R$_1$ and R$_1$' is, in some embodiments, at least about 1.05 moles per every 1 mole of isocyanate, or no more than about 1.2 moles (combined total of R$_1$ and R$_1$').

Any desired or effective solvent can be employed. Examples of suitable solvents include methylene chloride, tetrahydrofuran (THF), methyl ethyl ketone, toluene, dimethyl formamide, diethyl ether, hexane, ethyl acetate, and the like, and mixtures and combinations thereof.

The solvent can be present in any desired or effective amount, such as in an amount of at least about 10 milliliters of solvent per milimole of isocyanate, or at least about 15 milliliters of solvent per milimole of isocyanate, or at least about 20 milliliters of solvent per milimole of isocyanate.

The reaction between the isocyanate and the coupling agent can be carried out at any desired or effective temperature, such as from at least about 0° C. to no more than about 50° C., or from about 5° C. to about 40° C., or from about 15° C. to about 30° C.

The reaction can be carried out for any desired or effective period of time, such as for about 2 to about 12 hours, or from about 3 to about 10 hours, or from about 4 to about 6 hours.

Subsequent to completion of the reaction, the product can be treated by any desired or effective method, such as filtration of any solid by-products or washing the solution with water depending on the coupling agent used. The solvent can be removed by rotary evaporation. If needed, the product can be purified by washing with acetone and dried in a vacuum oven.

The molecular weight of the gellant may be measured by gel permeation chromatography (GPC), nuclear magnetic resonance imaging (NMR), or infrared spectroscopy (IR). GPC may also measure the range of molecular weight distribution. IR may also measure the purity of the gellant, because IR may show the disappearance of the diisocyanate peaks when the gellant is pure.

The gellant may have, for example, a number average molecular weight ($M_n$), as measured by gel permeation chromatography (GPC) of from about 1,000 to about 50,000, such as from about 2,000 to about 25,000, from about 3,000 to about 15,000, from about 6,000 to about 12,000, from about 1300 to about 7500, or from about 1450 to about 2200. The weight average molecular weight ($M_w$) of the resin may be 50,000 or less, such as, for example, from about 2,000 to about 50,000, from about 3,000 to about 40,000, from about 10,000 to about 30,000, from 1300 to about 7500, or from about 1450 to about 2200, as determined by GPC using polystyrene standards. The molecular weight of the gellant depends on the type of isocyanate and alcohol used. The molecular weight may also be determined by calculating the weight of the molecules used to form the gellant. The molecular weight distribution ($M_w/M_n$) of the gellant may be from about 1 to about 4, or from about 1 to about 3, or less than about 2.

Cationic Curable Monomer

Colored and colorless compositions, such as ink and overcoat compositions, respectively, may comprise at least one cationically curable monomer, that is, a monomer including at least one cationic polymerizable moiety in which the cationic moieties are, for example, epoxide, vinyl ether or oxetane groups. The term "curable monomer" is also intended to encompass curable oligomers, which may also be used in the compositions. Cationically curable monomers include cationically curable wax monomers.

The cationically curable monomer may be selected to provide an optimum rheology through curing in the presence of the remainder of the composition. In this regard, the cationically curable monomers may be, for example, epoxides, vinyl ethers or oxetanes. The cationically curable monomer may also be selected from epoxides and vinyl ethers. The cationically curable monomers may be chosen to be mono-, di- and/or multi-functional in order to obtain the desired rheology and image properties.

Among suitable monomers, the following may be specifically identified: 3,4-epoxycyclohexylmethyl-3,4-epoxycycloxane carboxylate; hexanedioic acid, bis[4-(vinyloxy)butyl] ester; bis[4-(ethenyloxy)butyl] adipate; 1,3-benzenedicarboxylic acid, bis[4-(ethenyloxy)butyl] ester; 4-(vinyloxy)butyl stearate; 4-(vinyloxy)butyl benzoate; 4-(vinyloxymethyl)cyclohexylmethyl benzoate; vinyl octadecyl ether; vinyl iso-octyl ether; 1,2,4-benzenetricarboxylic acid, tris[4-(ethenyloxy)butyl]ester; 1,4-butanediol diglycidyl ether; and 1,2-epoxyhexadecane.

In compositions comprising cationically curable monomers, the cationically curable monomer may be from about 65% to about 96% by weight of the composition, or from about 20% to about 48% by weight of the composition in which the composition additionally comprises at least one radically curable monomer in an amount from about 20% to about 48% by weight of the composition. In compositions comprising both cationically and radically curable monomers, the cationically curable monomer may be from about 20% to about 34% by weight of the composition, such as from about 20% to about 27% or from about 28% to about 34% by weight of the composition.

Cationic Photoinitiator

The colored and colorless compositions, such as ink compositions, may comprise at least one cationic photoinitiator that absorbs radiation at a wavelength and catalyzes a reaction as a result. In this regard, any suitable cationic photoinitiator may be used without limitation. There are many photoinitiators that can be used for cationic polymerization. The most commonly used cationic photoinitiators are triarylsulphonium and diaryliodonium salts, many of which are commercially available. Other similar type photoinitiators include aryldiazonium salts, triarylselenonium salts, dialkylphenacylsulphonium salts, triarylsulphoxonium salts, aryloxydiarylsulphonoxonium salts, and dialkylphenacylsulphoxonium salts. The salts are formed with ions such as $BF_4^-$, $PF_6^-$, $SbF_6^-$, $CF_3SO_3^-$, etc. Substitution is often introduced to the aryl groups in order to increase the solubility of the initiators in nonpolar media. Other specific examples of photoinitiators that may be mentioned include bis[4-(diphenylsulphonio)-phenyl] sulphide bis-hexafluorophosphate, bis[4-di(4-(2-hydroxyethyl)phenyl)sulphonio-phenyl] sulphide bis-hexafluorophosphate, bis[4-di(4-(2-hydroxyethyl)phenyl) sulphonio-phenyl] sulphide bishexafluoroantimonate, 4-methylphenyl-(4-(2-methylpropyl) phenyl)iodonium hexafluorophosphate, (4-bromophenyl)diphenylsulfonium triflate, (4-phenylthiophenyl)diphenylsulfonium triflate, and R-gen® BF-1172 (obtained from Chitec Chemical Co., Ltd., Taiwan).

The cationic photoinitiator may be used in amounts of about 20% or less by weight of the composition. The cationic photoinitiator may be from about 0.5% to about 10% by weight of the composition. The cationic photoinitiator should be stable up to at least the jetting temperature of the composition so as not to lose effectiveness following jetting and/or not to be prematurely reactive at the elevated jetting temperature.

The radiation to cationically cure the compositions may be provided by any of a variety of techniques, including but not limited to techniques making use of a xenon lamp, laser light, microwave energized V bulb, filtered light transported via light pipes from a D or H bulb, etc. The curing light may be filtered, if desired or necessary.

The curing of the ink following transfer to the image receiving substrate may be substantially complete, i.e., at least 75% of the cationically curable monomer is cured (reacted and/or crosslinked). This allows the composition to be substantially hardened, and thereby be much more scratch resistant than conventional unmodified wax based inks.

Radically Curable Monomer

Colored and colorless compositions, such as ink and overcoat compositions, respectively, optionally comprise at least one radically curable monomer. Examples of the radically curable monomer of the composition include propoxylated neopentyl glycol diacrylate (such as SR9003 from Sartomer), tricyclodecane diol diacrylate (such as SR833S from Sartomer), 1,6-hexanediol diacrylate (such as SR238 from Sartomer), diethylene glycol diacrylate, triethylene glycol diacrylate, hexanediol diacrylate, dipropyleneglycol diacrylate, tripropylene glycol diacrylate, alkoxylated neopentyl glycol diacrylate, isodecyl acrylate, tridecyl acrylate, isobornyl acrylate, propoxylated trimethylolpropane triacrylate, ethoxylated trimethylolpropane triacrylate, di-trimethylolpropane tetraacrylate, dipentaerythritol pentaacrylate, ethoxylated pentaerythritol tetraacrylate, propoxylated glycerol triacrylate, isobornyl methacrylate, lauryl acrylate, lauryl methacrylate, neopentyl glycol propoxylate methylether monoacrylate, isodecylmethacrylate, caprolactone acrylate, 2-phenoxyethyl acrylate, isooctylacrylate, isooctylmethacrylate, butyl acrylate, mixtures thereof and the like.

Here, the term "curable monomer" is also intended to encompass curable oligomers, which may also be used in the composition. Examples of suitable radically curable oligomers that may be used in the compositions have a low viscosity, for example, from about 50 mPa·s to about 10,000 mPa·s, such as from about 75 mPa·s to about 7,500 mPa·s or from about 100 mPa·s to about 5,000 mPa·s. Examples of such oligomers may include CN549, CN131, CN131B, CN2285, CN 3100, CN3105, CN132, CN133, CN 132, available from Sartomer Company, Inc., Exeter, Pa., Ebecryl 140, Ebecryl 1140, Ebecryl 40, Ebecryl 3200, Ebecryl 3201, Ebecryl 3212, available from Cytec Industries Inc, Smyrna Ga., PHOTOMER 3660, PHOTOMER 5006F, PHOTOMER 5429, PHOTOMER 5429F, available from Cognis Corporation, Cincinnati, Ohio, LAROMER PO 33F, LAROMER PO 43F, LAROMER PO 94F, LAROMER UO 35D, LAROMER PA 9039V, LAROMER PO 9026V, LAROMER 8996, LAROMER 8765, LAROMER 8986, available from BASF Corporation, Florham Park, N.J., and the like.

The radically curable monomer may include both a propoxylated neopentyl glycol diacrylate (such as SR-9003 from Sartomer) and a dipentaerythritol pentaacrylate (such as SR399LV from Sartomer). The inclusion of the pentaacrylate is advantageous in providing more functionality, and thus more reactivity, compared to the diacrylate. However, the amount of the pentaacrylate needs to be limited in the composition as too much can adversely affect the viscosity of the composition at application temperatures. The pentaacrylate thus makes up 10% by weight or less of the composition, such as 0.5 to 5% by weight of the composition.

The radically curable monomer may be included in the composition in an amount of, for example, from about 20% to about 48% by weight of the composition, or from about 20% to about 34% by weight of the composition, or from about 20% to about 27%.

Free-Radical Photoinitiator

The colored and colorless compositions, such as ink compositions, further optionally comprise at least one free-radical photoinitiator that absorbs radiation at a wavelength and catalyzes a reaction as a result. Examples of free-radical photoinitiators suitable for use with such compositions include acrylate and/or amide groups, include benzophenones, benzoin ethers, benzil ketals, α-hydroxyalkylphenones, and acylphosphine photoinitiators, such as sold under the trade designations of IRGACURE and DAROCUR from BASF. Specific examples of suitable free-radical photoinitiators include 2,4,6-trimethylbenzoyldiphenylphosphine oxide (available as BASF LUCIRIN TPO); 2,4,6-trimethylbenzoylethoxyphenylphosphine oxide (available as BASF LUCIRIN TPO-L); bis(2,4,6-trimethylbenzoyl)-phenylphosphine oxide (available as BASF IRGACURE 819) and other acyl phosphines; 2-methyl-1-(4-(methylthio)phenyl)-2-(4-morphorlinyl)-1-propanone (available as BASF IRGACURE 907) and 1-(4(2-hydroxyethoxy)phenyl)-2-hydroxy-2-methylpropan-1-one (available as BASF IRGACURE 2959); 2-hydroxy-1-(4-(4-(2-hydroxy-2-methylpropionyl)-benzyl)-phenyl)-2-methylpropan-1-one (available as BASF IRGACURE 127); titanocenes; isopropylthioxanthone (ITX); 1-hydroxy-cyclohexylphenylketone; benzophenone; 2,4,6-trimethylbenzophenone; 4-methylbenzophenone; diphenyl-(2,4,6-trimethylbenzoyl) phosphine oxide; 2,4,6-trimethylbenzoylphenylphosphinic acid ethyl ester; oligo(2-hydroxy-2-methyl-1-(4-(1-methylvinyl)phenyl) propanone); 2-hydroxy-2-methyl-1-phenyl-1-propanone; benzyl-dimethylketal; and mixtures thereof.

Amine synergists, that is, co-initiators, that donate a hydrogen atom to a free-radical photoinitiator and thereby form a radical species that initiates polymerization (amine synergists can also consume oxygen dissolved in the formulation—as oxygen inhibits free-radical polymerization its consumption increases the speed of polymerization), for example such as ethyl-4-dimethylaminobenzoate and 2-ethylhexyl-4-dimethylaminobenzoate, may also be included.

The photoinitiator package may include at least one alpha-hydroxy ketone photoinitiator and at least one phosphinoyl type photoinitiator(s). One example of the alpha-hydroxy ketone photoinitiator is IRGACURE 127, while one example of the phosphinoyl type photoinitiator is IRGACURE 819, both available from BASF. The ratio of the alpha-hydroxy ketone photoinitiator to the phosphinoyl type photoinitiator may be, for example, from about 90:10 to about 10:90, such as from about 80:20 to about 20:80 or from about 70:30 to about 30:70.

The total amount of the free-radical photoinitiator included in the composition may be, for example, from about 0 to about 10%, such as from about 0.5 to about 5%, by weight of the composition. The composition may be free of free-radical photoinitiators, for example, where e-beam radiation is used as the curing energy source for a free-radical curing.

The radiation to free-radical cure the compositions may be provided by any of a variety of techniques, including but not limited to techniques making use of a xenon lamp, laser light, microwave energized V bulb, filtered light transported via light pipes from a D or H bulb, etc. The curing light may be filtered, if desired or necessary.

Curable Wax

The compositions may also comprise at least one curable wax. A wax is solid at room temperature, specifically at 25° C. Inclusion of the wax thus may promote an increase in viscosity of the composition as it cools from the application temperature. Thus, the wax may also assist the gellant in avoiding bleeding of the composition through the substrate.

The curable wax may be any wax component that is miscible with the other components and that will polymerize with the curable monomer to form a polymer. The term wax includes, for example, any of the various natural, modified natural, and synthetic materials commonly referred to as waxes.

Suitable examples of curable waxes include those waxes that include or are functionalized with curable groups. The curable groups may include, for example, acrylate, methacrylate, alkene, allylic ether, epoxide, oxetane, and the like. These waxes can be synthesized by the reaction of a wax equipped with a transformable functional group, such as carboxylic acid or hydroxyl. The curable waxes described herein may be cured with the disclosed monomer(s).

Suitable examples of hydroxyl-terminated polyethylene waxes that may be functionalized with a curable group include, but are not limited to, mixtures of carbon chains with the structure $CH_3-(CH_2)_n-CH_2OH$, where there is a mixture of chain lengths, n, where the average chain length can be in the range of about 16 to about 50, and linear low molecular weight polyethylene, of similar average chain length. Suitable examples of such waxes include, but are not limited to, the UNILIN® series of materials such as UNILIN® 350, UNILIN® 425, UNILIN® 550 and UNILIN® 700 with $M_n$ approximately equal to 375, 460, 550 and 700 g/mol, respectively. All of these waxes are commercially available from Baker-Petrolite. Guerbet alcohols, characterized as 2,2-dialkyl-1-ethanols, are also suitable compounds. Exemplary Guerbet alcohols include those containing about 16 to about 36 carbons, many of which are commercially available from Jarchem Industries Inc., Newark, N.J. PRIPOL® 2033 (C-36 dimer diol mixture including isomers of the formula

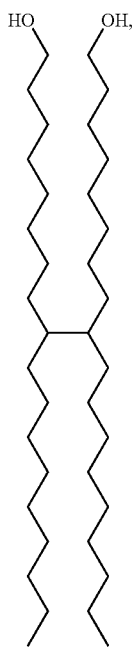

as well as other branched isomers that may include unsaturations and cyclic groups, available from Uniqema, New Castle, Del.); further information on $C_{36}$ dimer diols of this type is disclosed in, for example, "Dimer Acids," *Kirk-Othmer Encyclopedia of Chemical Technology*, Vol. 8, 4$^{th}$ Ed. (1992), pp. 223 to 237, the disclosure of which is totally incorporated herein by reference, may also be used. These alcohols can be reacted with carboxylic acids equipped with UV curable moieties to form reactive esters. Examples of these acids include acrylic and methacrylic acids, available from Sigma-Aldrich Co. These alcohols can also undergo transesterification reactions with esters containing UV curable moieties, such as methyl 3,4-epoxycyclohexane carboxylate

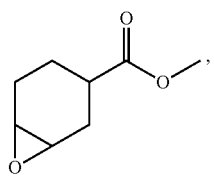

which is commercially available from Synasia.

Suitable examples of carboxylic acid-terminated polyethylene waxes that may be functionalized with a curable group include mixtures of carbon chains with the structure $CH_3$—$(CH_2)_n$—COOH, where there is a mixture of chain lengths, n, where the average chain length is about 16 to about 50, and linear low molecular weight polyethylene, of similar average chain length. Suitable examples of such waxes include, but are not limited to, UNICID® 350, UNICID® 425, UNICID® 550 and UNICID® 700 with $M_n$ equal to approximately 390, 475, 565 and 720 g/mol, respectively. Other suitable waxes have a structure $CH_3$—$(CH_2)_n$—COOH, such as hexadecanoic or palmitic acid with n=14, heptadecanoic or margaric or daturic acid with n=15, octadecanoic or stearic acid with n=16, eicosanoic or arachidic acid with n=18, docosanoic or behenic acid with n=20, tetracosanoic or lignoceric acid with n=22, hexacosanoic or cerotic acid with n=24, heptacosanoic or carboceric acid with n=25, octacosanoic or montanic acid with n=26, triacontanoic or melissic acid with n=28, dotriacontanoic or lacceroic acid with n=30, tritriacontanoic or ceromelissic or psyllic acid, with n=31, tetratriacontanoic or geddic acid with n=32, pentatriacontanoic or ceroplastic acid with n=33. Guerbet acids, characterized as 2,2-dialkyl ethanoic acids, are also suitable compounds. Exemplary Guerbet acids include those containing 16 to 36 carbons, many of which are commercially available from Jarchem Industries Inc., Newark, N.J. PRIPOL® 1009 (C-36 dimer acid mixture including isomers of the formula

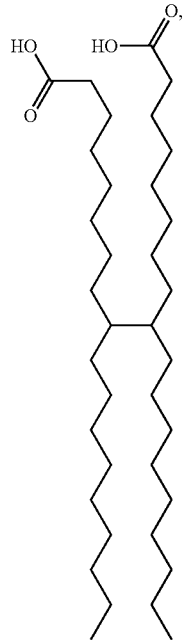 [SMILES: CCCCCCCCCC(CCCCCCCC(=O)O)C(CCCCCCCCC)CCCCCCCC(=O)O]

as well as other branched isomers that may include unsaturations and cyclic groups, available from Uniqema, New Castle, Del.; further information on $C_{36}$ dimer acids of this type is disclosed in, for example, "Dimer Acids," *Kirk-Othmer Encyclopedia of Chemical Technology*, Vol. 8, 4$^{th}$ Ed. (1992), pp. 223 to 237, the disclosure of which is totally incorporated herein by reference, can also be used. These carboxylic acids can be reacted with alcohols equipped with UV curable moieties to form reactive esters. Examples of these alcohols include, but are not limited to, 2-allyloxyethanol from Sigma-Aldrich Co.;

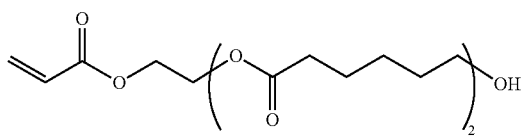

SR495B from Sartomer Company, Inc.;

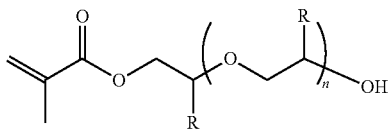

CD572 (R=H, n=10) and SR604 (R=Me, n=4) from Sartomer Company, Inc.;

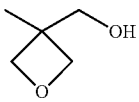

3-methyl-3-oxetane methanol from Sigma-Aldrich Co.; and

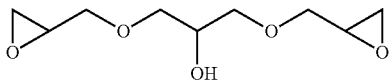 [SMILES: OC(COCC1CO1)COCC1CO1]

glycerol diglycidyl ether from Sigma-Aldrch Co.

The curable wax can be included in the composition in an amount of from, for example, about 0.1% to about 30% by weight of the composition, such as from about 0.5% to about 20% or from about 0.5% to 15% by weight of the composition.

Stabilizer

The colored and colorless compositions may also optionally comprise an antioxidant stabilizer. The optional antioxidants of the compositions protect the images from oxidation and also protect the composition components from oxidation during the heating portion of an ink preparation process. Specific examples of suitable antioxidant stabilizers include NAUGARD™ 524, NAUGARD™ 635, NAUGARD™ A, NAUGARD™ 1-403, and NAUGARD™ 959, commercially available from Crompton Corporation, Middlebury, Conn.; IRGANOX™ 1010, and IRGASTAB UV 10, commercially available from BASF Specialty Chemicals; GENORAD 16 and GENORAD 40 commercially available from Rahn AG, Zurich, Switzerland, and the like.

Additives

The colored and colorless compositions may further optionally comprise conventional additives to take advantage of the known functionality associated with such conventional additives. Such additives may include, for example, defoamers, surfactants, slip and leveling agents, etc.

The colored and colorless compositions desirably do not yellow upon curing, with little to no measurable difference in any of L*a*b* values or k, c, m, y being observed. Being "substantially non-yellowing" refers to a composition changing color or hue upon curing in an amount of less than about 15%, such as less than about 10% or less than about 5%, for example about 0%.

Colorant

Colored compositions, such as phase change ink compositions, may comprise at least one colorant. Any desired or effective colorant can be employed in the phase change ink compositions, including dyes, pigments, mixtures thereof, and the like, provided that the colorant can be dissolved or dispersed in the ink carrier. Any dye or pigment may be chosen, provided that it is capable of being dispersed or dissolved in the ink carrier and is compatible with the other ink components. The phase change carrier compositions can be used in combination with conventional phase change ink colorant materials, such as Color Index (C.I.) Solvent Dyes, Disperse Dyes, modified Acid and Direct Dyes, Basic Dyes, Sulphur Dyes, Vat Dyes, and the like. Examples of suitable dyes include Neozapon Red 492 (BASF); Orasol Red G (BASF); Direct Brilliant Pink B (Oriental Giant Dyes); Direct Red 3BL (Classic Dyestuffs); Supranol Brilliant Red 3BW (Bayer AG); Lemon Yellow 6G (United Chemie); Light Fast Yellow 3G (Shaanxi); Aizen Spilon Yellow C-GNH (Hodogaya Chemical); Bernachrome Yellow GD Sub (Classic Dyestuffs); Cartasol Brilliant Yellow 4GF (Clariant); BASFnon Yellow 2GN (BASF); Orasol Black CN (BASF); Savinyl Black RLSN (Clariant); Pyrazol Black BG (Clariant); Morfast Black 101 (Rohm & Haas); Diaazol Black RN (ICI); Orasol Blue GN (BASF); Savinyl Blue GLS (Clariant); Luxol Fast Blue MBSN (Pylam Products); Sevron Blue 5GMF (Classic Dyestuffs); Basacid Blue 750 (BASF); Neozapon Black X51 (BASF); Classic Solvent Black 7 (Classic Dyestuffs); Sudan Blue 670 (C.I. 61554) (BASF); Sudan Yellow 146 (C.I. 12700) (BASF), Sudan Red 462 (C.I. 26050) (BASF); C.I. Disperse Yellow 238, Neptune Red Base NB543 (BASF, C.I. Solvent Red 49); Neopen Blue FF-4012 from BASF; Lampronol Black BR from ICI (C.I. Solvent Black 35); Morton Morplas Magenta 36 (C.I. Solvent Red 172); metal phthalocyanine colorants such as those disclosed in U.S. Pat. No. 6,221,137, the disclosure of which is totally incorporated herein by reference, and the like. Polymeric dyes can also be used, such as those disclosed in, for example, U.S. Pat. Nos. 5,621,022 and 5,231,135, the disclosures of each of which are herein entirely incorporated herein by reference, and commercially available from, for example, Milliken & Company as Milliken Ink Yellow 869, Milliken Ink Blue 92, Milliken Ink Red 357, Milliken Ink Yellow 1800, Milliken Ink Black 8915-67, uncut Reactant Orange X-38, uncut Reactant Blue X-17, Solvent Yellow 162, Acid Red 52, Solvent Blue 44, and uncut Reactant Violet X-80.

Pigments are also suitable colorants for the phase change inks. Examples of suitable pigments include PALIOGEN Violet 5100 (commercially available from BASF); PALIOGEN Violet 5890 (commercially available from BASF); HELIOGEN Green L8730 (commercially available from BASF); LITHOL Scarlet D3700 (commercially available from BASF); SUNFAST Blue 15:4 (commercially available from Sun Chemical); Hostaperm Blue B2G-D (commercially available from Clariant); Hostaperm Blue B4G (commercially available from Clariant); Permanent Red P-F7RK; Hostaperm Violet BL (commercially available from Clariant); LITHOL Scarlet 4440 (commercially available from BASF); Bon Red C (commercially available from Dominion Color Company); ORACET Pink RF (commercially available from BASF); PALIOGEN Red 3871 K (commercially available from BASF); SUNFAST Blue 15:3 (commercially available from Sun Chemical); PALIOGEN Red 3340 (commercially available from BASF); SUNFAST Carbazole Violet 23 (commercially available from Sun Chemical); LITHOL Fast Scarlet L4300 (commercially available from BASF); SUNBRITE Yellow 17 (commercially available from Sun Chemical); HELIOGEN Blue L6900, L7020 (commercially available from BASF); SUNBRITE Yellow 74 (commercially available from Sun Chemical); SPECTRA PAC C Orange 16 (commercially available from Sun Chemical); HELIOGEN Blue K6902, K6910 (commercially available from BASF); SUNFAST Magenta 122 (commercially available from Sun Chemical); HELIOGEN Blue D6840, D7080 (commercially available from BASF); Sudan Blue OS (commercially available from BASF); NEOPEN Blue FF4012 (commercially available from BASF); PV Fast Blue B2GO1 (commercially available from Clariant); IRGALITE Blue BCA (commercially available from BASF); PALIOGEN Blue 6470 (commercially available from BASF); Sudan Orange G (commercially available from Aldrich), Sudan Orange 220 (commercially available from BASF); PALIOGEN Orange 3040 (BASF); PALIOGEN Yellow 152, 1560 (commercially available from BASF); LITHOL Fast Yellow 0991 K (commercially available from BASF); PALIOTOL Yellow 1840 (commercially available from BASF); NOVOPERM Yellow FGL (commercially available from Clariant); Ink Jet Yellow 4G VP2532 (commercially available from Clariant); Toner Yellow HG (commercially available from Clariant); Lumogen Yellow D0790 (commercially available from BASF); Suco-Yellow L1250 (commercially available from BASF); Suco-Yellow D1355 (commercially available from BASF); Suco Fast Yellow D1 355, D1 351 (commercially available from BASF); HOSTAPERM Pink E 02 (commercially available from Clariant); Hansa Brilliant Yellow 5GX03 (commercially available from Clariant); Permanent Yellow GRL 02 (commercially available from Clariant); Permanent Rubine L6B 05 (commercially available from Clariant); FANAL Pink D4830 (commercially available from BASF); CINQUASIA Magenta (commercially available from DU PONT); PALIOGEN Black L0084 (commercially available from BASF); Pigment Black K801 (commercially available from BASF); and carbon blacks such as REGAL 330™ (commercially available from Cabot), Nipex 150 (commercially available from Evonik) Carbon Black 5250 and Carbon Black 5750 (commercially available from Columbia Chemical), and the like, as well as mixtures thereof.

Also suitable are the colorants disclosed in U.S. Pat. Nos. 6,472,523, 6,726,755, 6,476,219, 6,576,747, 6,713,614, 6,663,703, 6,755,902, 6,590,082, 6,696,552, 6,576,748, 6,646,111, 6,673,139, 6,958,406, 6,821,327, 7,053,227, 7,381,831, and 7,427,323, the disclosures of each of which are incorporated herein by reference in their entirety.

Preparing Compositions

Compositions may be prepared by mixing the composition components at a temperature of from about 75° C. to about 120° C., such as from about 80° C. to about 110° C. or from about 75° C. to about 100° C., until homogenous, for example for from about 0.1 hour to about 3 hours, such as about 2 hours. Once the mixture is homogenous, then any photoinitiator may be added. Alternatively, all of the components of the composition may be combined immediately and mixed together.

In ink compositions, the gellant and cationically curable monomer (and the radically curable monomer in hybrid ink compositions) assist in evoking a rapid, thermally driven phase change that pins an ink composition to a substrate before curing, effectively limiting the amount of showthrough observed on the substrate (e.g., plain paper). These components also impart a large substrate latitude to ink compositions, including coated papers, foils, and plastics. In the absence of a colorant, these same phase change systems can be used to prevent a digitally applied overcoat from soaking into areas of a substrate uncovered by a printed image.

Cationic curing offers advantages over radical curing, at least radical curing alone, including providing to a colored or colorless composition any of increased thermal stability, insensitivity to oxygen, low shrinkage and opportunities for dark cure and/or shadow cure. Dark cure refers to the phenomenon in which polymerization continues after radiation is discontinued. It is enabled by the fact that cationic curing is initiated by photoacids and, therefore, does not undergo termination reactions, as radicals do. Shadow cure refers to the phenomenon in which active curing centers migrate after radiation is discontinued and, in the process, continue the polymerization process in areas that had not been exposed to radiation. Both dark and shadow curing offer the potential for an increased degree of polymerization over systems which do not offer dark and/or shadow curing. Specifically, both dark and shadow curing offer the potential for an increased degree of polymerization in pigmented systems in which photons are reflected, scattered and/or absorbed by particles, preventing them from penetrating through the entire composition. Hybrid curable inks offer the speed of radical curing combined with the dark and/or shadow curing properties of cationic polymerization pathways.

Radiation-Curable Gel Inks

Radiation-curable gel inks may be prepared by any suitable technique. For example, the inks may be prepared by mixing the initiator, monomer, gellant, and the curable wax; and heating the mixture to obtain a single phase with low viscosity. Thereafter the hot mixture is slowly added to a heated colorant (i.e. pigment) dispersion (which may be a concentrate) while agitating the mixture. The ink composition may then be filtered, optionally at an elevated temperature, through a filter to remove extraneous particles.

The method of preparation for the ink compositions may be modified so as to accommodate the type of reactive gelling agents used for the preparation of the ink compositions. For example, a concentrate of the gelling agent may be prepared in one of the components of the ink composition prior to the addition of the other components. Solutions containing co-gelling agents can also be prepared by a method similar to the one described above.

The ink compositions may have gelling temperatures of from about 30° C. to about 75° C., such as from about 30° C. to about 70° C., or from about 35° C. to about 70° C., or from about 45° C. to about 70° C., or at about 65° C. In particular, the ink composition is a gel at room temperature.

When the ink composition is in the gel state, the viscosity of the ink composition is at least about 1,000 mPa·s, such as at least about 10,000 mPa·s, or at least about 100,000 mPa·s. The viscosity values in the gel state of exemplary ink compositions may be in the range of from about $10^3$ to about $10^9$ mPa·s, such as from about $10^{4.5}$ to about $10^{6.5}$ mPa·s. Gel-phase viscosity of embodiments can vary with the print process. For example, the highest viscosities may be suitable for use in exemplary embodiments that employ intermediate transfer, or when jetting directly to porous paper in order to minimize the effects of ink bleed and feathering. On the other hand, less porous substrates, such as plastic, may require lower viscosities that control dot gain and agglomeration of individual ink pixels. The gel viscosity can be controlled by ink composition and substrate temperature. An additional benefit of the gel state for radiation-curable gellant-containing ink compositions is that higher viscosities of about $10^3$-$10^4$ mPa·s can reduce oxygen diffusion, which in turn leads to a faster rate of cure in free-radical initiation.

101111 The desired viscosity depends on the temperature. When the ink composition is at jetting temperature, the ink composition may have a viscosity of less than about 15 mPa·s, such as less than about 12 mPa·s, or from about 3 to about 12 mPa·s, or from about 5 to about 10 mPa·s. In some embodiments, the ink compositions are jetted at temperatures of less than about 100° C., such as from about 40° C. to about 100° C., or from about 55° C. to about 90° C., less than about 80° C., such as from about 60° C. to about 80° C., such as about 70° C.

In general, the viscosity is about 10 mPa·s or less at a jetting temperature from about 85° C. to about 95° C. The viscosity should sharply increase, as demonstrated below in Table 1, around the transition temperature of about 65° C. The viscosity is from about $10^5$ to about $10^6$ mPa·s at a temperature of about 30° C. and below.

The gel ink when printed on paper may have a mass of from about 0.1 to about 1.5 mg/cm$^2$ or from about 0.4 to about 0.7 mg/cm$^2$.

The gel ink may contain any combination of elements, as long as it meets physical properties encompassed by this disclosure.

Image Forming and Inkjet Devices

Gel ink jet printing process and apparatuses are well known in the art and may include either direct or indirect image formation.

Printed images may be generated with the ink described herein by incorporating the ink into an inkjet device, such as a thermal inkjet device, an acoustic inkjet device, or a piezoelectric inkjet device, and concurrently causing droplets of molten ink to be ejected in an imagewise manner onto a substrate. The ink may be heated to a jetting temperature, for instance, above the gel-transition temperature of the ink composition.

The substrate may be at any suitable temperature during recording. The recording substrate may be at room temperature. However, in some embodiments, the substrate may be heated or cooled to have a surface temperature that is, for example, within the range of gel-phase transition temperatures for the ink composition. For example, the substrate may be maintained at a temperature of from about 5° C. to about 160° C., such as from about 15° C. to about 50° C., or from about 20° C. to about 40° C. In this way, the jetted ink may be made to rapidly form a gel.

The ink is typically included in at least one reservoir connected by any suitable feeding device to the ejecting channels and orifices of the inkjet head. In the jetting procedure, the inkjet head may be heated, by any suitable method, to the jetting temperature of the inks. The ink reservoir(s) may also include heating elements to heat the ink. The UV inks are thus transformed from the gel state to a molten state for jetting. "At least one" or "one or more," as used to describe components of the inkjet device, such as the ejecting channels, orifices, etc., refers to from 1 to about 2 million, such as from about 1000 to about 1.5 million, or about 10,000 to about 1 million of any such component found in the inkjet device. "At least one" or "one or more" as used to describe other components of the inkjet device such as the inkjet head, reservoir, feeder, etc., refers to from 1 to about 15, such as from 1 to about 8, or from 1 to about 4 of any such component found in the inkjet device.

The inks may also be employed in indirect (offset) printing ink jet applications, where droplets of the melted ink are ejected in an imagewise manner onto an intermediate transfer member and the ink in the imagewise pattern is subsequently transferred from the intermediate transfer member to a final recording substrate. An exemplary offset or indirect printing process is also disclosed in U.S. Pat. No. 5,389,958, the entire disclosure of which is incorporated herein by reference.

The intermediate-transfer member may take any suitable form, such as a drum or belt. The member surface may be at room temperature or may be heated to have a surface temperature, for example, within the gel-state temperature range for the ink composition. For example, the surface may be maintained at a temperature of about 25° C. to about 100° C., such as from about 30° C. to about 70° C., or from about 30° C. to about 50° C. In this way, the jetted ink may be made to rapidly form a gel, which gel is maintained on the surface of the transfer member until transfer to the image-receiving substrate. Thus, the ink may be heated to a jetting temperature, for instance, above the gel-transition temperature of the ink composition and then heated to a second temperature at which the gel forms that is less than the first temperature.

Once upon the intermediate-transfer member surface, the jetted ink may be exposed to a limited extent of radiation so as to effect a limited curing of the ink upon the intermediate-transfer member surface. This intermediate curing does not fully cure the ink, but merely assists in setting the jetted ink so that it may be transferred to the image receiving substrate with the appropriate amount of penetration, which requires the ink droplets to have a certain rheology before transfer. For controlling the extent of the curing if an intermediate cure is practiced, reference is made to U.S. Pat. No. 7,270,408 and co-pending U.S. Patent Application Publication No. 2006/0119686, each incorporated herein by reference. This intermediate-curing step is not necessary in embodiments in which the gel state is sufficient to impart the desired rheology to the ink droplets.

Following jetting to the intermediate-transfer member and optional intermediate curing thereon, the ink composition is then transferred to a suitable substrate.

The ink can be jetted or transferred onto any suitable substrate or recording sheet to form an image including plain papers such as XEROX 4200 papers, XEROX Image Series papers, Courtland 4024 DP paper, ruled notebook paper, bond paper, and the like; silica coated papers such as Sharp Company silica coated paper, JuJo paper, HAMMERMILL LASERPRINT paper, and the like; glossy coated papers such as XEROX Digital Color Gloss, Sappi Warren Papers LUSTROGLOSS, and the like; transparency materials; fabrics; textile products; plastics; polymeric films; inorganic substrates such as metals, ceramics, and wood; and the like.

Following transfer to the substrate or jetting to the substrate if direct printing is employed, the ink is cured by exposing the image on the substrate to radiation. For example, radiation having an appropriate wavelength, mainly the wavelength at which the ink initiator absorbs radiation, may be used. This initiates the curing reaction of the ink composition. The radiation exposure need not be long, and may occur from about 0.05 to about 10 seconds, such as from about 0.2 to about 2 seconds. The exposure times are more often expressed as substrate speeds of the ink composition passing under a UV lamp. For example, the microwave energized, doped mercury bulbs available from UV Fusion are placed in an elliptical mirror assembly that is 10 cm wide; multiple units may be placed in series. Thus, a belt speed of 0.1 ms$^{-1}$ would require 1 second for a point on an image to pass under a single unit, while a belt speed 4.0 ms$^{-1}$ would require 0.2 seconds to pass under four bulb assemblies.

The energy source used to initiate crosslinking of the radiation-curable components of the composition may be actinic, such as radiation having a wavelength in the ultraviolet or visible region of the spectrum; accelerated particles, such as electron beam radiation; thermal, such as heat or infrared radiation; or the like. Actinic radiation provides excellent control over the initiation and rate of crosslinking. Suitable sources of actinic radiation include mercury lamps, xenon lamps, carbon arc lamps, tungsten filament lamps, lasers, light emitting diodes, sunlight, electron beam emitters and the like. The curing light may be filtered or focused, if desired or necessary.

The curable components of the ink composition react to form a cured or cross-linked network of appropriate hardness and robustness. The curing may be substantially complete to complete, i.e., at least 75% of the curable components are cured (reacted and/or cross-linked). This allows the ink composition to be substantially hardened and much more scratch resistant, and also adequately controls the amount of show-through on the substrate.

EXAMPLES

This disclosure will be illustrated further in the following Examples.

Four compounds of interest were generated, starting with the commercially available dimer diisocyanate (DDI) as a starting material (from Cognis Corporation):

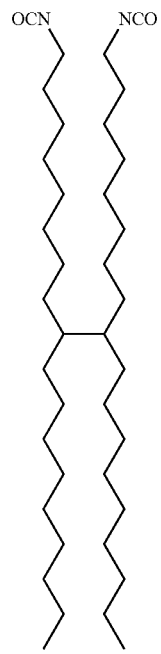

Dimer diisocyanate (DDI)

monobenzylcapped DDI (1):

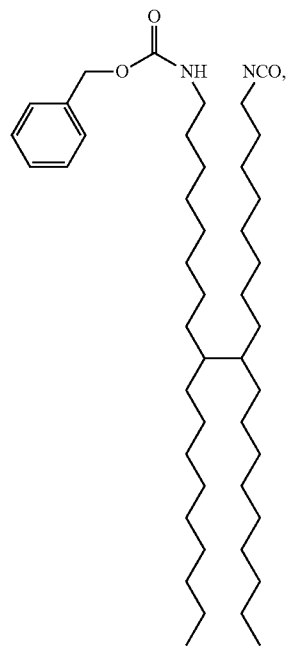

AB dicapped DDI (2):

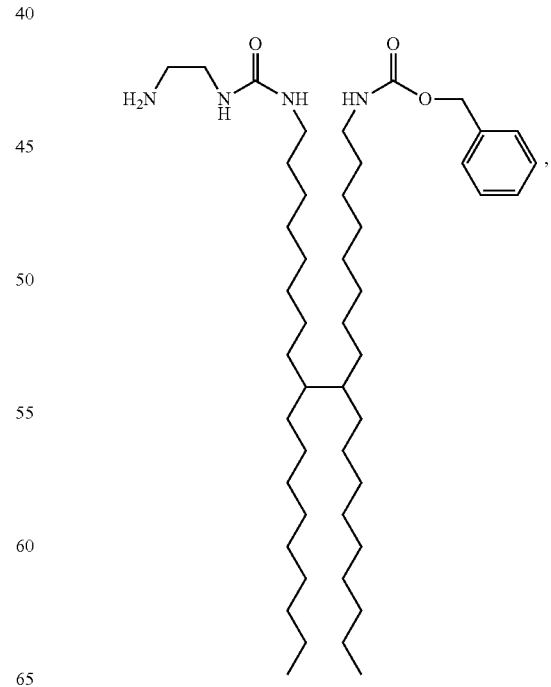

urea-urethane dimer (3)
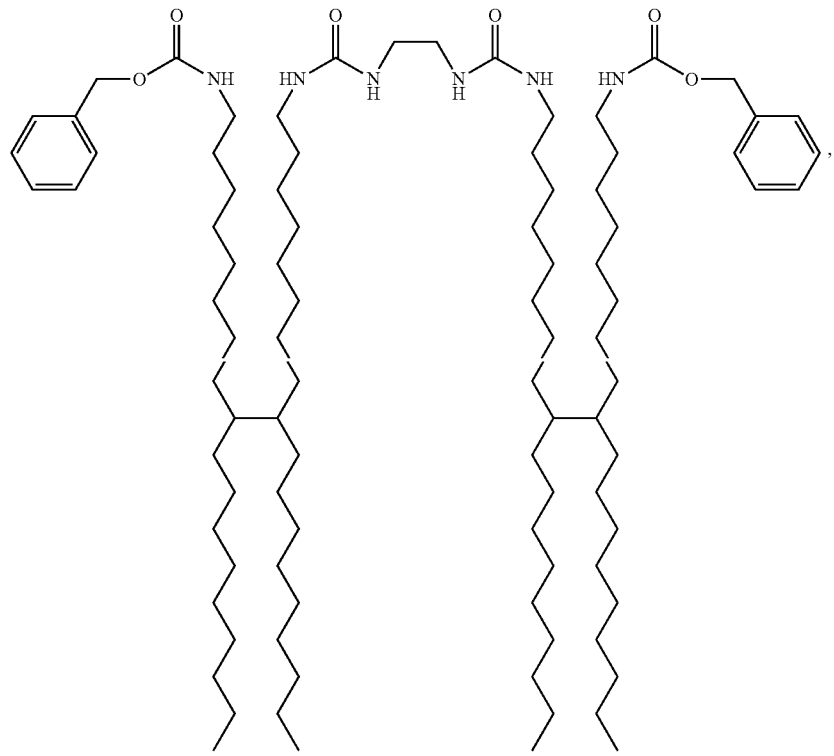 [SMILES: CCCCCCCCCC(CCCCCCCCNC(=O)NCCNC(=O)NCCCCCCCCC(CCCCCCCCC)C(CCCCCCCCC)CCCCCCCCNC(=O)OCc1ccccc1)C(CCCCCCCCC)CCCCCCCCNC(=O)OCc1ccccc1]
and
urea-urethane trimer (4)
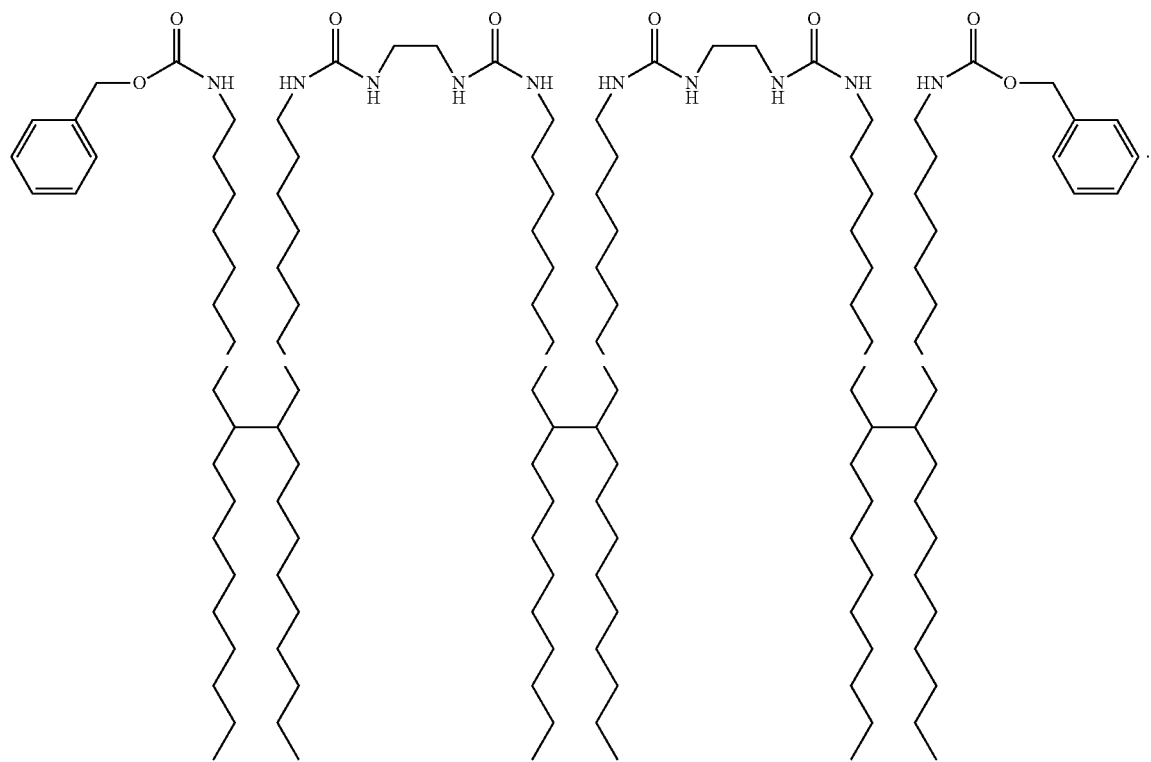 [SMILES: CCCCCCCCCC(CCCCCCCCNC(=O)NCCNC(=O)NCCCCCCCCC(CCCCCCCCC)C(CCCCCCCCC)CCCCCCCCNC(=O)OCc1ccccc1)C(CCCCCCCCC)CCCCCCCCNC(=O)NCCNC(=O)NCCCCCCCCC(CCCCCCCCC)C(CCCCCCCCC)CCCCCCCCNC(=O)OCc1ccccc1]

Example 1

Preparation of Monobenzyl-Capped DDI (1)

An AB-dicapped diisocyanate was prepared by the following method.

Dimer diisocyanate (20 g, 34 mmol, obtained from Cognis Corporation) was added to a 1 L round bottom flask equipped with a magnetic stir bar followed by THF solvent (300 mL). The mixture was stirred until dissolved. Next, benzyl alcohol (3.53 mL, 34 mmol, obtained from Sigma-Aldrich Corporation) was added followed by dibutyltin dilaurate (0.202 mL, 0.34 mmol, obtained from Sigma-Aldrich Corporation). The reaction was heated to reflux (80° C.) for 5 hours and the THF solvent was removed from the reaction by rotary evaporation. Compound 1 (23 g, 33 mmol, 97% yield) was isolated as a viscous syrup $^1$H NMR spectroscopy showed that the product was consistent with the structure of monobenzyl-capped DDI (1).

Example 2

Preparation of Ab-Dicapped DDI (2)

Monobenzyl-capped DDI (1) (10 g, 14.34 mmol) was dissolved in THF solvent (400 mL) with stirring. Next, ethylenediamine (1.146 mL, 16.98 mmol) was slowly added dropwise. The reaction was stirred overnight at room temperature. A low viscosity jelly was observed. The THF was removed from the reaction by rotary evaporation to to produce AB-dicapped DDI (2) product (12.58 g, 16.61 mmol, 98% yield) as a sticky orange product. $^1$H NMR spectroscopy showed that the product was consistent with the structure of AB-dicapped DDI (2).

Example 3

Preparation of Urea-Urethane Dimer (b 3)

Monobenzyl capped DDI (1) (10 g, 14.38 mmol) was added to a 500 mL round bottom flask equipped with a magnetic stir bar, followed by THF (400 mL) and the mixture was stirred until dissolved. Next, ethylenediamine (0.484 mL, 7.17 mmol) was added dropwise to the reaction. The reaction was stirred overnight at room temperature. The reaction contents became a jelly. The THF was removed by rotary evaporation to yield urea-urethane dimer (3) (10.3 g, 7.08 mmol, 99% yield) as a soft gel. $^1$H NMR spectroscopy showed that the product was consistent with the structure of urea-urethane dimer (3).

Example 4

Preparation of Urea-Urethane Trimer (4)

AB-dicapped DDI (2) (8.31 mL, 10.97 mmol) was added to a 1 L round bottom flask equipped with a magnetic stir bar followed by THF (500 mL) and the mixture was stirred till dissolved. Next, DDI (3.50 mL, 5.49 mmol) was added dropwise to the reaction. The reaction viscosity went up sharply. When the DDI was added, a gel had formed in the reaction. The reaction was stirred at room temperature overnight to produce a clear, viscous solution. The THF was removed by rotary evaporation to yield urea-urethane gellant trimer (9.8 g, 4.66 mmol, 85% yield) as a clear, colorless, hard resin. $^1$H NMR spectroscopy showed that the product was consistent with the structure of urea-urethane trimer (4).

Viscosity Testing

Viscosity of the gellants was tested in liquid vehicles to determine their rheological profiles and suitability for ink applications. It is desirable that inks containing gellants exhibit rapid phase transition and rapid rise in viscosity. If the phase transition is not fast enough, the ink bleeds or soaks through the paper.

The urea-urethane dimer and trimer gellants of Examples 3 and 4 were dissolved in SR9003 acrylate monomer and Unilin-350 acrylate wax and their viscosity was tested over a range of temperatures. The formulations are givein in Example 5 (dimer) Example 6 (trimer), and the results are summarized below in Table 1. Generally, these urea-urethane gellants demonstrated an unexpectedly high viscosity. Therefore, inks containing these urethane-urea gellants may allow a wider viscosity latitude over the ester-terminated polyamide gellants used in UV curable inks.

Example 5

Urea-Urethane Dimer Formulated with Monomer and Wax

| Compound | Parts |
| --- | --- |
| Urea-urethane dimer (3) | 7.5 |
| Unilin 350-acrylate | 5.0 |
| SR9003 monomer | 87.5 |

Example 6

Urea-Urethane Trimer Formulated with Monomer and Wax

| Compound | Parts |
| --- | --- |
| Urea-urethane trimer (4) | 7.5 |
| Unilin 350-acrylate | 5.0 |
| SR9003 monomer | 87.5 |

TABLE 1

| Temperature (° C.) | Complex Viscosity (mPa · s) | |
| --- | --- | --- |
| | Example 5 (dimer) | Example 6 (trimer) |
| 90 | 9.75 | 8.25 |
| 85 | 9.49 | 7.76 |
| 80 | 22.9 | 10.1 |
| 75 | 68.3 | 15.5 |
| 70 | $1.08 \times 10^2$ | 23.3 |
| 65 | $1.49 \times 10^2$ | 33.3 |
| 60 | $1.09 \times 10^3$ | $1.58 \times 10^2$ |
| 55 | $1.17 \times 10^4$ | $2.04 \times 10^3$ |
| 50 | $3.02 \times 10^4$ | $6.42 \times 10^3$ |
| 45 | $6.02 \times 10^4$ | $1.91 \times 10^4$ |
| 40 | $1.01 \times 10^5$ | $4.22 \times 10^4$ |
| 35 | $1538941.54 \times 10^5$ | $7.91 \times 10^4$ |
| 30 | $2.23 \times 10^5$ | $1.24 \times 10^5$ |

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also encompassed by the following claims.
What is claimed is:
1. A urea-urethane gellant comprising at least one of the following compounds:
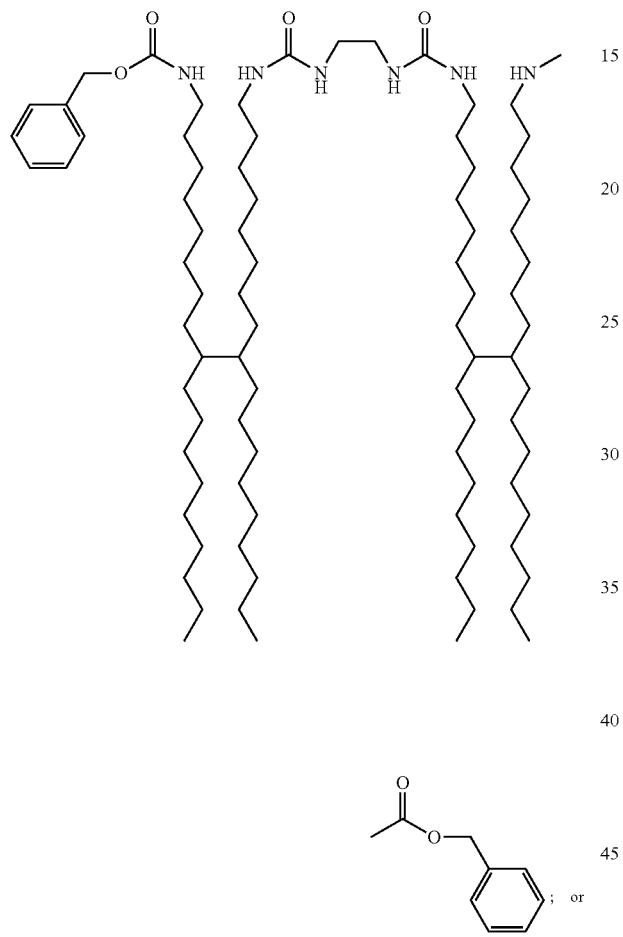
; or
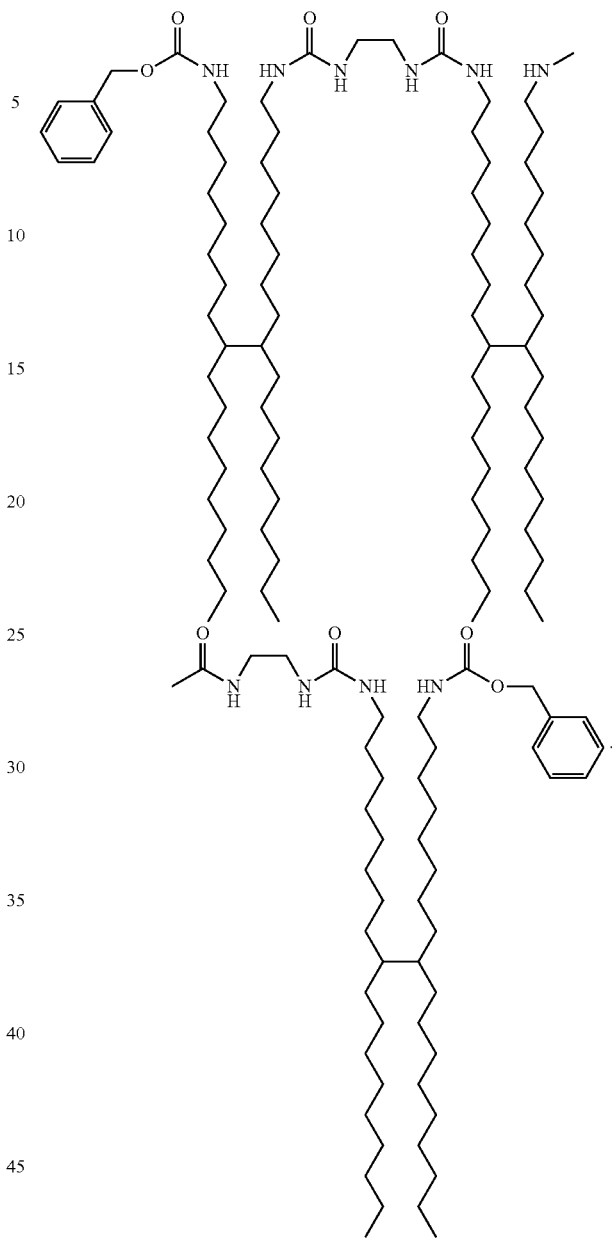
2. The gellant of claim 1, wherein the gellant comprises:
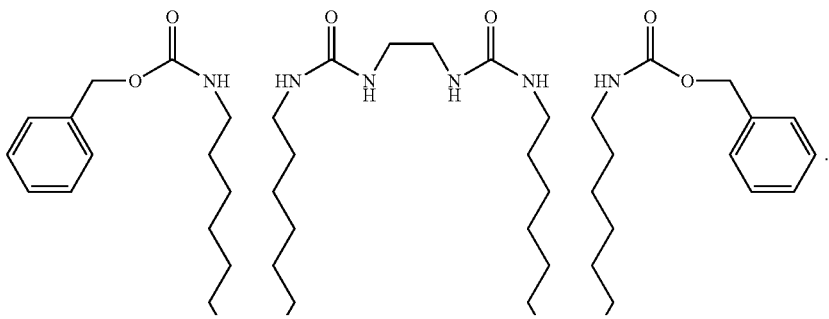

-continued
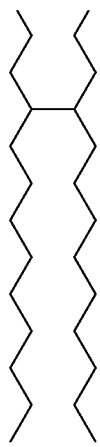 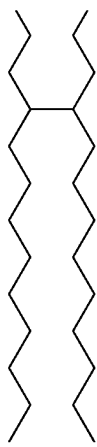
3. The gellant of claim 1, wherein the gallant comprises:
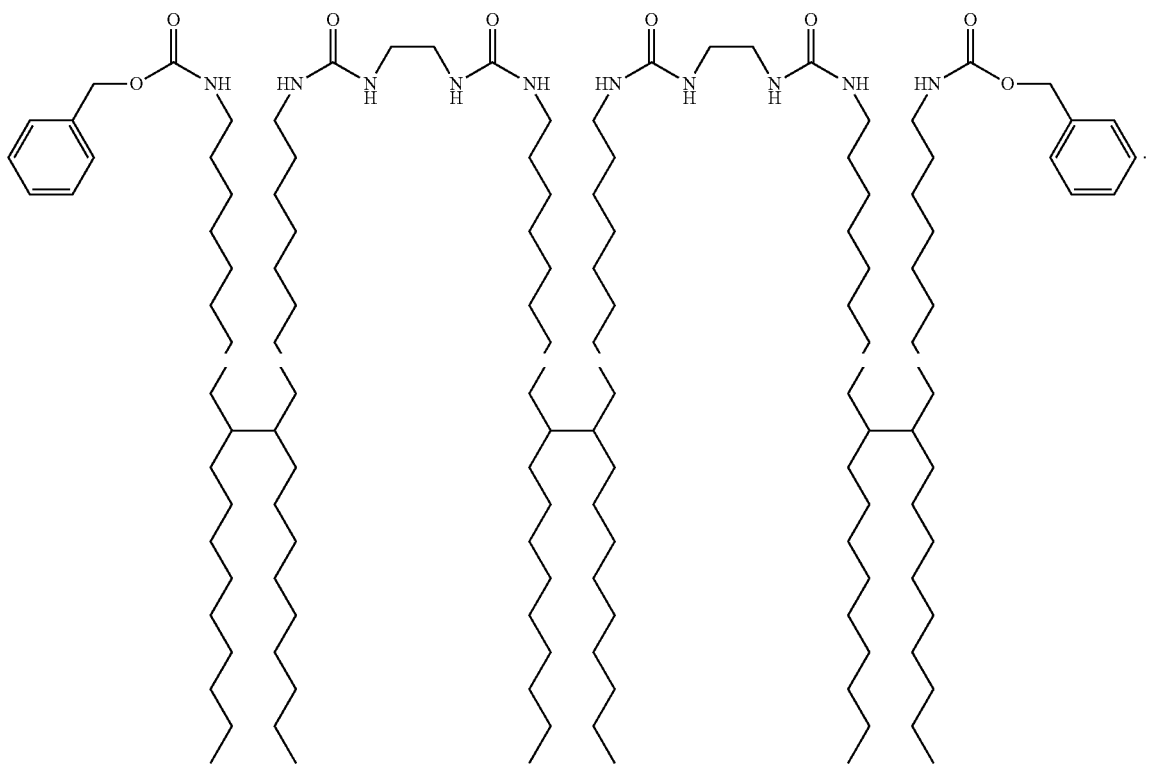 [SMILES: CCCCCCCCCC(CCCCCCCCNC(=O)NCCNC(=O)NCCCCCCCCC(CCCCCCCCC)C(CCCCCCCCC)CCCCCCCCNC(=O)OCc1ccccc1)C(CCCCCCCCC)CCCCCCCCNC(=O)NCCNC(=O)NCCCCCCCCC(CCCCCCCCC)C(CCCCCCCCC)CCCCCCCCNC(=O)OCc1ccccc1]

4. The gellant of claim 1, wherein the gellant has a molecular weight distribution of less than 2.

5. A method of preparing an organic gellant, the method comprising:
adding an isocyanate, an alcohol or a diamine, and a solvent to a reaction vessel;
stirring the reaction vessel;
isolating an intermediate product from the reaction vessel; and
converting the intermediate product to the organic gellant, wherein
the organic gellant comprises at least one of the following compounds:

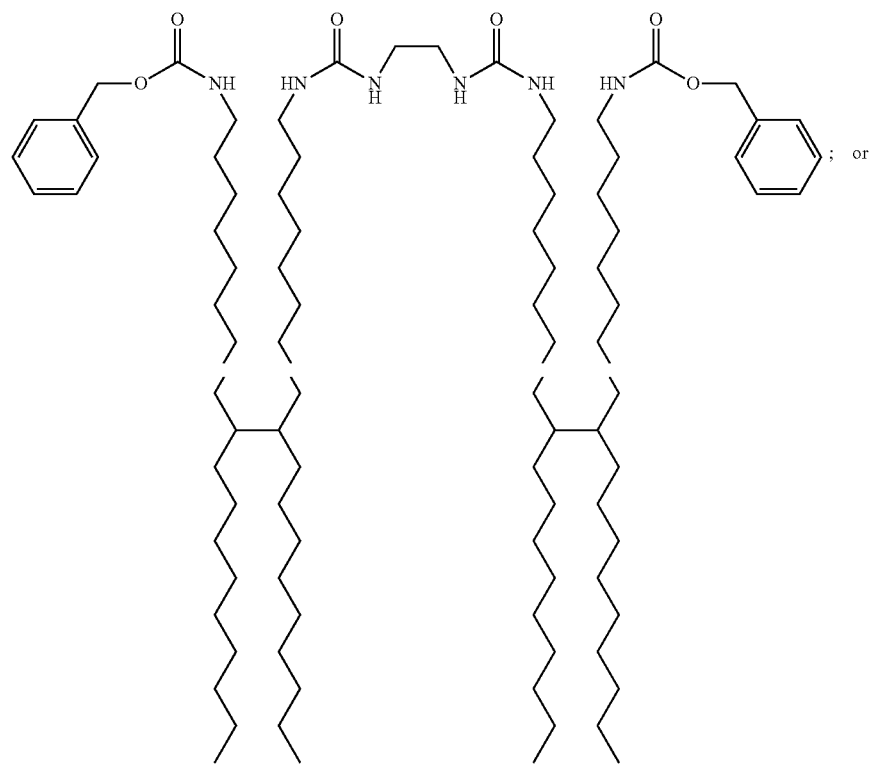 [SMILES: CCCCCCCCCC(CCCCCCCCNC(=O)NCCNC(=O)NCCCCCCCCC(CCCCCCCCC)C(CCCCCCCCC)CCCCCCCCNC(=O)OCc1ccccc1)C(CCCCCCCCC)CCCCCCCCNC(=O)OCc1ccccc1]

; or

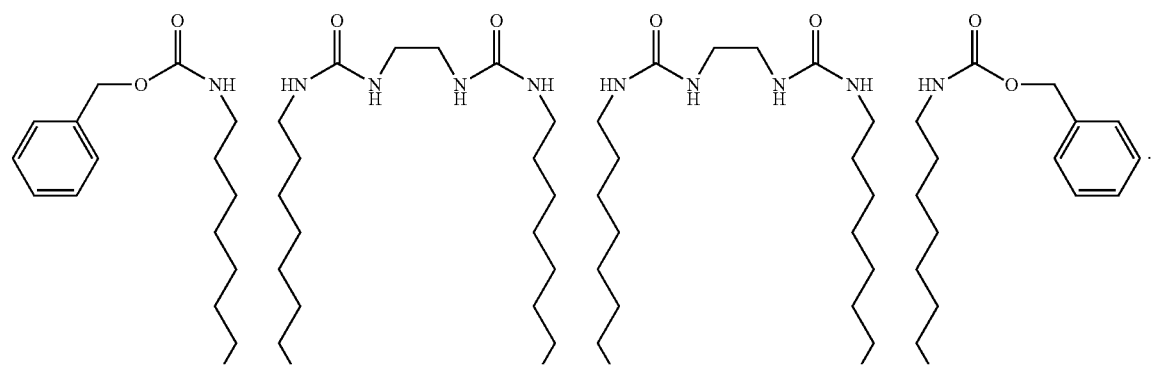

.

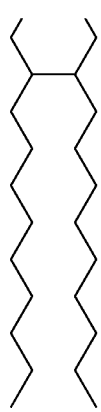
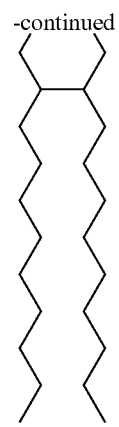

6. The method of claim 5, wherein a first end of the isocyanate reacts with the alcohol and a second end of the isocyanate reacts with a first end of the diamine.

7. The method of claim 6, wherein a second end of the diamine is combined with the intermediate product.

8. The method of claim 5, wherein the isocyanate is a dimer diisocyanate.

9. The method of claim 5, wherein the isocyanate is a monobenzyl capped dimer diisocyanate.

10. The method of claim 5, wherein the isocyanate is an EDA-benzyl alcohol capped dimer diisocyanate.

11. The method of claim 5, wherein the organic gellant is a compound of the formula:

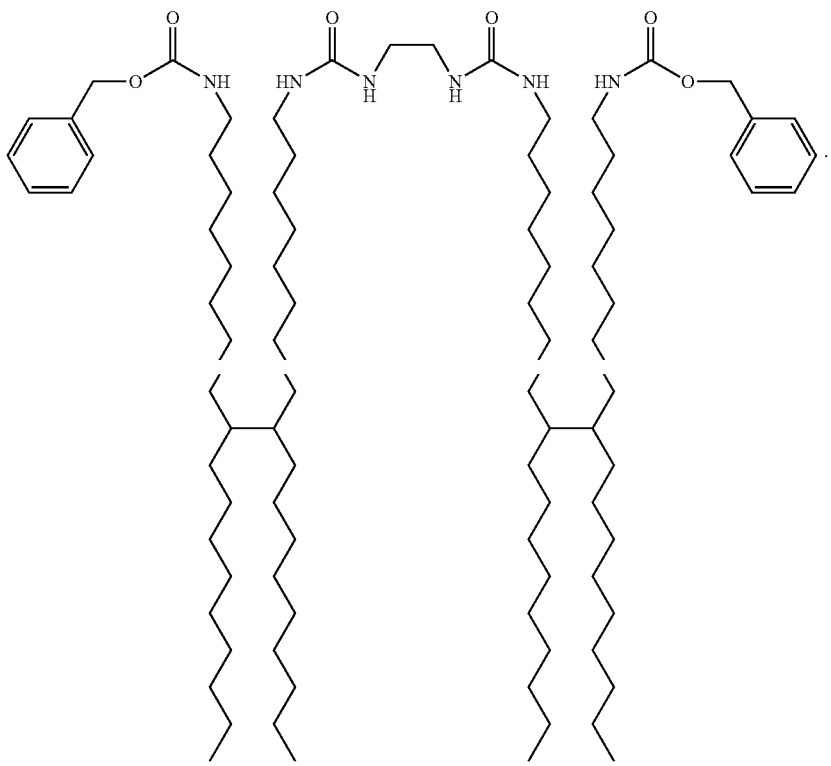

12. The method of claim 5, wherein the organic gellant is a compound of the formula:

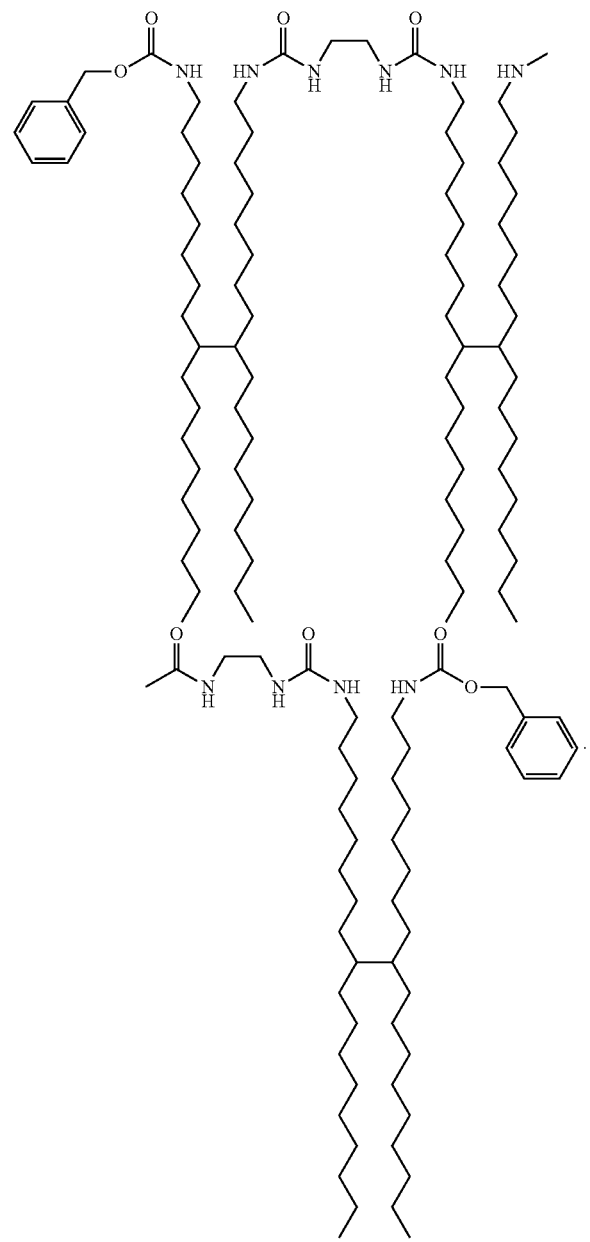

13. The gellant of claim 1 having
a molecular weight distribution of less than 2; and
a viscosity of the gellant dissolved in a fluid with wax is from about 8 mPa·s to about $2.20 \times 10^5$ mPa·s at a temperature of about 30° C. to about 95° C.

14. The gellant of claim 13, wherein the viscosity of the gellant mixture is less than 20 mPa·s at a temperature of about 85° C. to about 95° C. and $10^5$ mPa·s to about $10^6$ mPa·s at a temperature less than about 30° C.

15. A radiation-curable gel ink, comprising:
a curable monomer,
an organic gellant,
an optional gel-forming wax,
an optional photoinitiator, and
an optional colorant, wherein
the organic gellant comprises at least one of the following compounds:

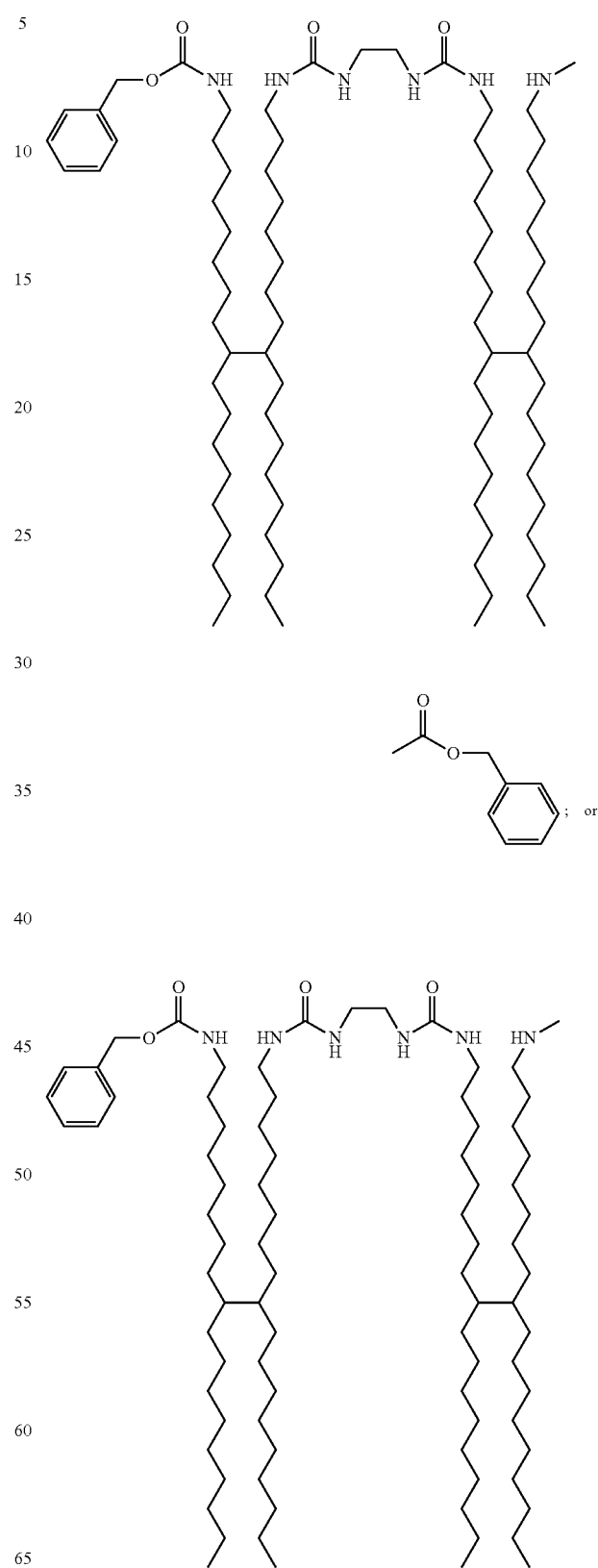

-continued
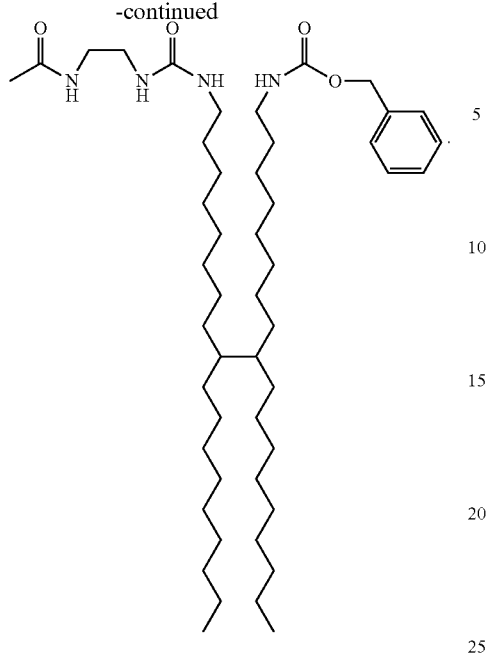
16. The ink of claim 15, wherein the gellant has a molecular weight distribution of less than 2.
* * * * *